United States Patent
Zhang et al.

(10) Patent No.: US 11,411,184 B2
(45) Date of Patent: Aug. 9, 2022

(54) COMPOUND, DISPLAY PANEL, AND DISPLAY APPARATUS

(71) Applicant: Wuhan Tianma Micro-Electronics Co., Ltd., Wuhan (CN)

(72) Inventors: Lei Zhang, Wuhan (CN); Wei Gao, Wuhan (CN); Jinghua Niu, Wuhan (CN); Yang Li, Wuhan (CN); Yan Lu, Wuhan (CN); Gaojun Huang, Wuhan (CN)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 483 days.

(21) Appl. No.: 16/352,663

(22) Filed: Mar. 13, 2019

(65) Prior Publication Data
US 2020/0212308 A1 Jul. 2, 2020

(30) Foreign Application Priority Data

Dec. 28, 2018 (CN) .................. 201811622667.X

(51) Int. Cl.
*H01L 51/00* (2006.01)
*H01L 51/50* (2006.01)
(Continued)

(52) U.S. Cl.
CPC ........ *H01L 51/0067* (2013.01); *C07D 251/24* (2013.01); *C07D 401/10* (2013.01);
(Continued)

(58) Field of Classification Search
None
See application file for complete search history.

(56) References Cited

U.S. PATENT DOCUMENTS

2006/0113905 A1* 6/2006 Nakamura .......... H01L 27/3244
313/511

FOREIGN PATENT DOCUMENTS

| CN | 107074784 | A |   | 8/2017 |
| CN | 108129386 | A | * | 6/2018 |
| KR | 20170134252 | A |   | 12/2017 |

OTHER PUBLICATIONS

Park et al. (ACS Appl. Mater. Interfaces 2017, 9, p. 2693).*
(Continued)

*Primary Examiner* — Jay Yang
(74) *Attorney, Agent, or Firm* — Alston & Bird LLP

(57) ABSTRACT

An organic compound can be applied as a host material for an OLED display device. The compound has a structure represented by Formula (I):

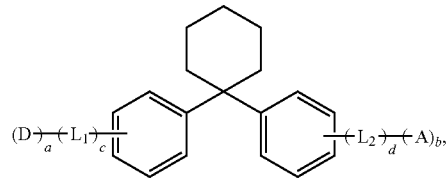

Formula (I)

a and b, being independently 1, 2 or 3, respectively represent the numbers of electron donor D and electron acceptor A; c and d, independently being 0, 1, or 2, respectively representing the numbers of group $L_1$ and group $L_2$. D, $L_1$ and $L_2$ are each alkyl, cycloalkylene, heterocyclic group, aryl, heteroaryl, fused aryl, or fused heteroaryl; and A is selected from nitrogen-containing heterocyclic substituents, cyano-containing substituents, triaryl-boron-derived substituents, and phos-
(Continued)

phoxy-containing substituents. The compound has a D-(π)-σ-(π)-A structure with bipolarity, and the σ bond can interrupt an intramolecular charge transfer between D and A, so that the excited state is limited to a local excited state in moiety of D or A, and the compound has a small excited-state dipole moment.

16 Claims, 2 Drawing Sheets

(51) Int. Cl.
    *C07D 401/14*      (2006.01)
    *C07D 401/10*      (2006.01)
    *C07D 251/24*      (2006.01)

(52) U.S. Cl.
    CPC ........ *C07D 401/14* (2013.01); *H01L 51/0061* (2013.01); *H01L 51/0072* (2013.01); *H01L 51/0073* (2013.01); *H01L 51/0074* (2013.01); *H01L 51/5036* (2013.01); *H01L 51/5016* (2013.01); *H01L 51/5056* (2013.01); *H01L 51/5072* (2013.01)

(56) References Cited

OTHER PUBLICATIONS

Machine English translation of Lu et al. (CN-108129386 A). Aug. 24, 2021.*
CN Office Action, dated Aug. 20, 2021.

* cited by examiner

COMPOUND, DISPLAY PANEL, AND DISPLAY APPARATUS

CROSS-REFERENCE TO RELATED APPLICATIONS

The present application claims priority to Chinese Patent Application No. CN201811622667.X filed on Dec. 28, 2018 the content of which is incorporated herein by reference in its entirety.

TECHNICAL FIELD

The present disclosure relates to the technical field of organic electroluminescent materials, and particularly, to an electroluminescent compound, a display panel and a display apparatus containing the compound.

BACKGROUND

As a new generation of display technology, the organic electroluminescent materials such as OLEDs have been widely used in flat-panel displays, flexible displays, solid-state lighting and vehicle displays, due to their advantages of being ultrathin, being self-luminous, and having a wide viewing angle, fast response, high luminous efficiency, good temperature adaptability, simple manufacturing process, low driving voltage, low energy consumption and the like.

Light emitted by the OLEDs can be classified into electro-fluorescence and electro-phosphorescence depending upon the luminescence mechanism. Fluorescence is emission light resulted from a radiation attenuation transition of singlet excitons, and phosphorescence is emission light resulted from a radiation attenuation of triplet excitons to the ground state. According to the spin quantum statistics theory, a forming probability ratio of singlet excitons to triplet excitons is 1:3. The internal quantum efficiency of the electro-fluorescent materials is no more than 25%, and the external quantum efficiency thereof is generally even less than 5%. Theoretically, the internal quantum efficiency of the electro-phosphorescent materials can reach 100%, and the external quantum efficiency thereof can be up to 20%. In 1998, Professor Yuguang Ma from Jilin University in China and Professor Forrest from Princeton University in the United States respectively reported ruthenium (Ru) complexes and platinum complexes that were used as dyes doped into the light-emitting layer, successfully obtained and explained a phenomenon of phosphorescence electroluminescence for the first time, and pioneered the application of the phosphorescent materials to an electroluminescent device.

The long lifetime (in μs) of phosphorescent heavy metal materials may lead to triplet state-triplet state quenching and concentration quenching at high current densities and further result in a degradation of device performance. Therefore, phosphorescent heavy metal materials are usually doped into suitable host materials to form a host-guest doping system. In this way, energy transfer is optimized, and luminous efficiency and lifetime are maximized. At present, the commercialization of heavy metal doping materials is mature, and it is difficult to develop alternative doping materials. Thus, developing a novel phosphorescent host material is becoming a new research topic.

SUMMARY

In a first aspect, the present disclosure provides a compound having a D-(π)-σ-(π)-A structure. The compound has a chemical structure represented by a Formula (I):

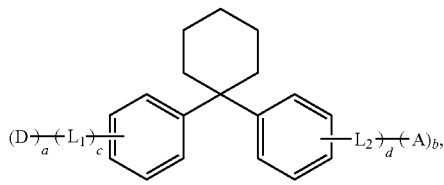

Formula (I)

wherein D represents an electron donor, A represents an electron acceptor, a is a number of an electron donor D, b is a number of an electron acceptor A, and a and b are each 1, 2, or 3 independently, c is a number of a group $L_1$, d is a number of a group $L_2$, and c and d are each 0, 1, or 2 independently, $L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocycloalkylene, a substituted or unsubstituted C6-C40 arylene, a substituted or unsubstituted C4-C40 heteroarylene, a substituted or unsubstituted C10-C60 fused arylene, and a substituted or unsubstituted C10-C60 fused heteroarylene, when c or d is 2, the two $L_1$ or the two $L_2$ are identical or different;

the electron donor D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and a derivative group thereof, a substituted or unsubstituted C12-C40 diphenylamino and a derivative group thereof, and a substituted or unsubstituted C12-C40 acridinyl and a derivative group thereof, when a is 2 or 3, the two or three electron donors D are identical or different, the electron acceptor A is selected from the group consisting of nitrogen-containing heterocyclic substituents, cyano-containing substituents, triaryl-boron-derived substituents, and phosphoxy-containing substituents, and when b is 2 or 3, the two or three electron acceptors A are identical or different.

In a second aspect, the present disclosure provides a display panel, comprising an organic light-emitting device, wherein the organic light-emitting device comprises an anode, a cathode disposed oppositely to the anode, and a light-emitting layer disposed between the anode and the cathode, wherein the light-emitting layer comprises a host material and a guest material, and the host material is one or more compounds in the first aspect.

In a third aspect, the present disclosure provides a display panel, comprising an organic light-emitting device, wherein the organic light-emitting device comprises an anode, a cathode disposed oppositely to the anode, a capping layer disposed on a side of the cathode facing away from the anode, and an organic layer disposed between the anode and the cathode, the organic layer comprises an electron transmission layer, a hole transmission layer, and a light-emitting layer, and at least one of the capping layer, the electron transmission layer, the hole transmission layer, and the light-emitting layer is made of the compound in the first aspect.

In a fourth aspect, the present disclosure provides a display apparatus including the above display panel.

The compound having the D-(π)-σ-(π)-A structure according to the present disclosure is a bipolar material, which can replace the conventional D-π-A skeleton known in the prior art. The conventional D-π-A bipolar material with a large dipole moment $\mu_s$ may present a strong intramolecular charge transfer. The D-(π)-σ-(π)-A structure of the compound according to the present disclosure has bipolarity, and the intermediate σ bond can effectively interrupt the intramolecular charge transfer between the electron donor D and the electron acceptor A, so that the excited state is limited as a local excited state in moiety of the electron donor D or the electron acceptor A, and thus the compound has a small excited-state dipole moment. In this way, the compound, when used as host material of a light-emitting layer of an OLED device, can effectively reduce an efficiency roll-off of a blue light material and enhance the brightness and luminous efficiency.

The compound according to the present disclosure, which is used as the host material in an electroluminescent device, has a high triplet energy level $E_T$, a large molecular density, a high glass transition temperature and a high molecular thermal stability, and thus can effectively improve an equilibrium migration of carriers and widen a recombination area of excitons. In this regard, the external quantum efficiency (EQE) and service life of the device are effectively enhanced. Therefore, the compound according to the present disclosure can be well applied in the electroluminescent device field.

DESCRIPTION OF EMBODIMENTS

Figure 1:
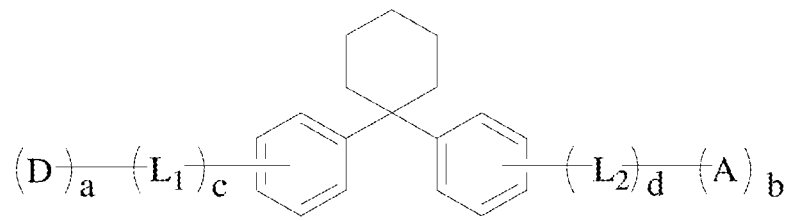
FIG. 1 is a chemical formula of a compound according to the present disclosure.

The present disclosure is described in detail with aid of embodiments and comparative examples. The following embodiments are merely used to illustrate the present disclosure, but not intended to limit the scope of the present disclosure. Any modification or equivalent replacement with respect to the technical solutions of the present disclosure without departing from the scope of the present disclosure shall fall into the protection scope of the present disclosure.

In a first aspect, the present disclosure provides a compound having a chemical structure represented by a Formula (I):

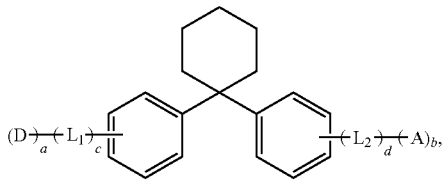

Formula (I)

in which D represents an electron donor, A represents an electron acceptor, a is a number of the electron donor D, b is a number of the electron acceptor A, and a and b are each 1, 2, or 3 independently, c is a number of the group $L_1$, d is a number of the group $L_2$, c and d are each 0, 1, or 2 independently, $L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocycloalkylene, a substituted or unsubstituted C6-C40 arylene, a substituted or unsubstituted C4-C40 heteroarylene, a substituted or unsubstituted C10-C60 fused arylene, and a substituted or unsubstituted C10-C60 fused heteroarylene, the electron donor D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and a derivative group thereof, a substituted or unsubstituted C12-C40 diphenylamino and a derivative group thereof, and a substituted or unsubstituted C12-C40 acridityl and a derivative group thereof, and the electron acceptor A is selected from the group consisting of a nitrogen-containing heterocyclic substituents, cyano-containing substituents, triaryl-boron-derived substituents, and phosphoxy-containing substituents.

The D-(π)-σ-(π)-A structure of the compound according to the present disclosure also has bipolarity, and the intermediate σ bond can effectively interrupt the intramolecular charge transfer between the electron donor D and the electron acceptor A, so that the excited state is limited to a local excited state in moiety of the electron donor D or the electron acceptor A, and thus the compound has a mall excited-state dipole moment. In this way, the compound, when used as host material of a light-emitting layer of an OLED device, can effectively reduce an efficiency roll-off of a blue light material and enhance the luminous brightness and luminous efficiency.

The compound according to the present disclosure, which is used as the host material in the electroluminescent device, has a high triplet energy level $E_T$, a large molecular density, a high glass transition temperature and a high molecular thermal stability, and thus can effectively improve an equilibrium migration of carriers, widen a recombination area of excitons, and effectively improve light extraction efficiency. In this regard, the external quantum efficiency (EQE) and service life of the device are effectively enhanced. Therefore, the compound according to the present disclosure can be well applied in the electroluminescent device field.

According to an embodiment of the compound of the present disclosure, the electron donor D is further selected from the following groups:

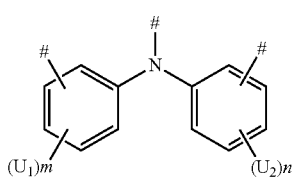

-continued

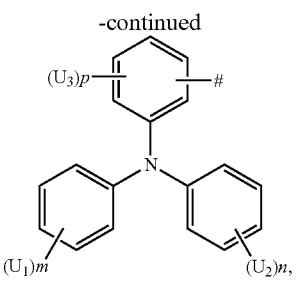

in which m, n and p are each independently 0, 1, 2, or 3, $U_1$, $U_2$ and $U_3$ are each independently selected from the group consisting of hydrogen, a substituted or unsubstituted C1-C30 alkyl, a substituted or unsubstituted silicylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl, and represents a bonding position.

According to an embodiment of the compound of the present disclosure, the electron donor D is further selected from the following groups:

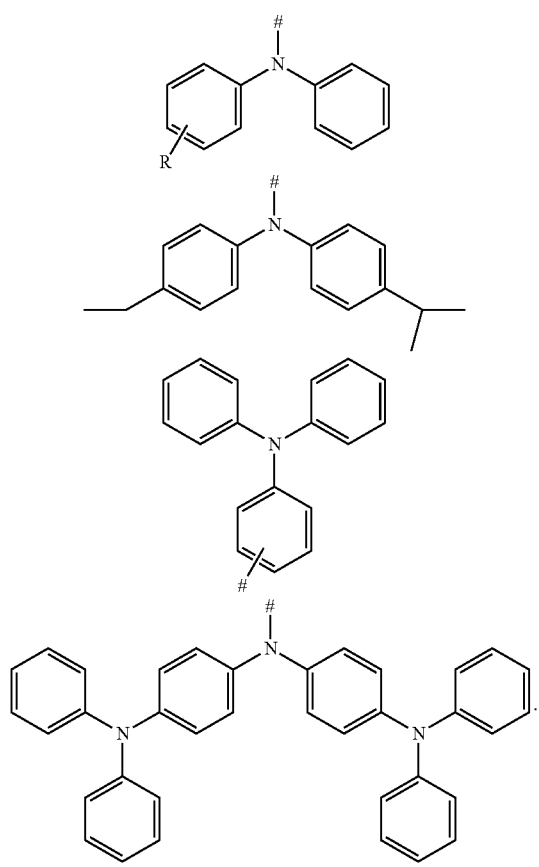

in which R is selected from the group consisting of hydrogen, a substituted or unsubstituted C1-C20 alkyl, a substituted or unsubstituted silicylene, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C10-C30 fused aryl, and a substituted or unsubstituted C4-C40 hetero aryl.

According to an embodiment of the compound of the present disclosure, the electron donor D is further selected from the following groups:

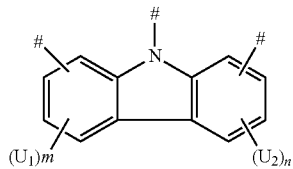

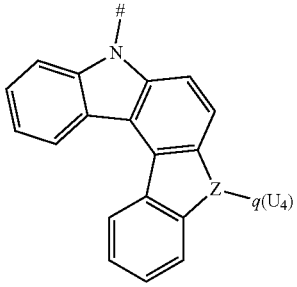

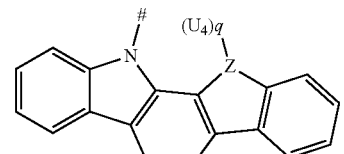

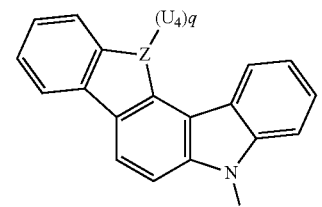

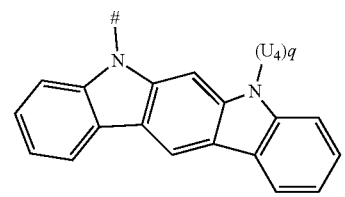

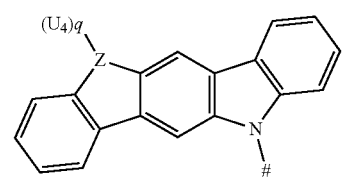

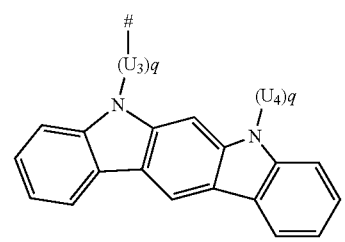

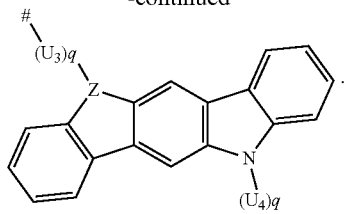

in which Z is carbon, nitrogen, oxygen, sulfur, or silicon, m, n and p are each independently 0, 1, 2, or 3, $U_2$, $U_3$ and $U_4$ are each independently selected from the group consisting of hydrogen, a substituted or unsubstituted C1-C30 alkyl, a substituted or unsubstituted silicylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl, when Z is oxygen or sulfur, q is 0, and # represents a bonding position.

According to an embodiment of the compound of the present disclosure, the electron donor D is further selected from the following groups:

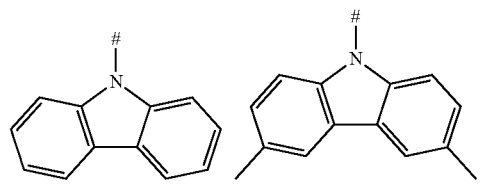

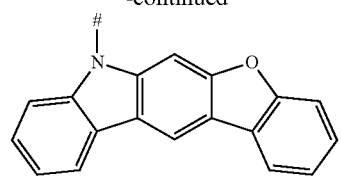

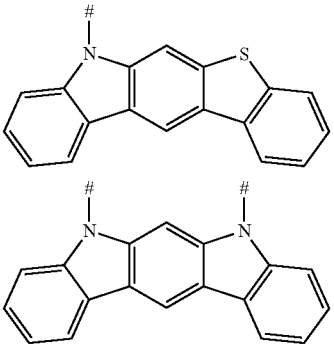

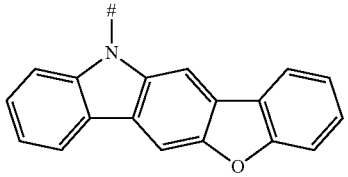

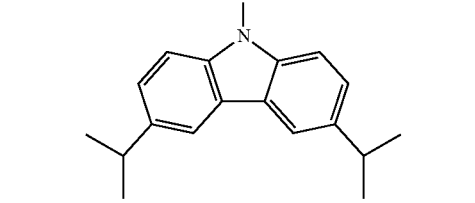

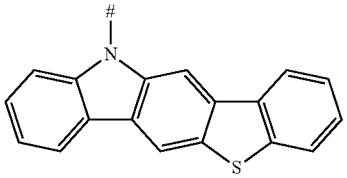

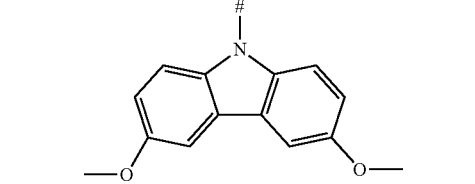

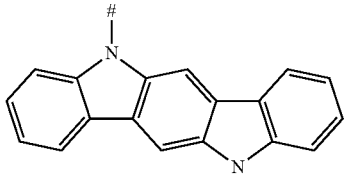

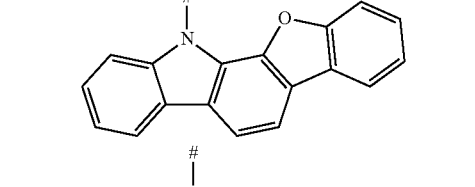

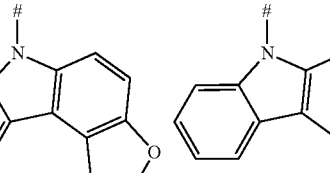

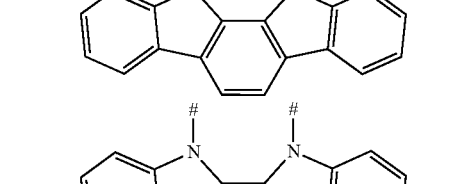

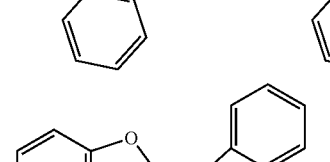

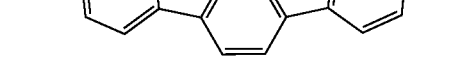

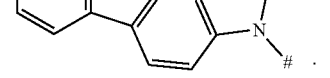

According to an embodiment of the compound of the present disclosure, the electron donor D is further selected from the following groups:

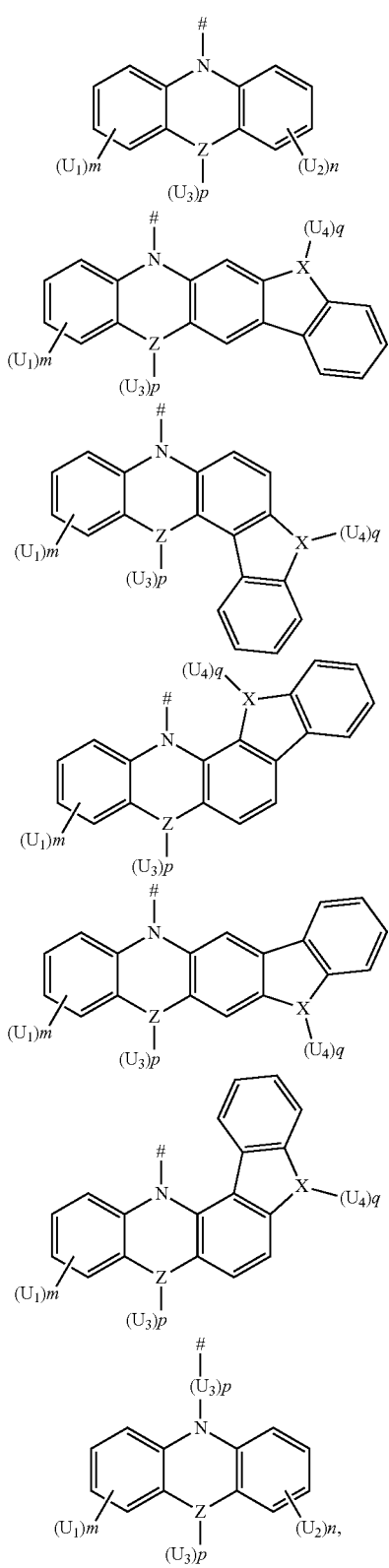

in which Z is carbon, nitrogen, oxygen, sulfur, or silicon, X is carbon, nitrogen, oxygen, or sulfur, m, n, p and p are each independently 0, 1, 2, or 3, $U_1$, $U_2$, $U_3$ and $U_4$ are each independently selected from the group consisting of hydrogen, a substituted or unsubstituted C1-C30 alkyl, a substituted or unsubstituted silicylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl, when Z is oxygen or sulfur, p is 0, when X is oxygen or sulfur, q is 0, and represents a bonding position.

According to an embodiment of the compound of the present disclosure, the electron donor D is further selected from the following groups:

-continued

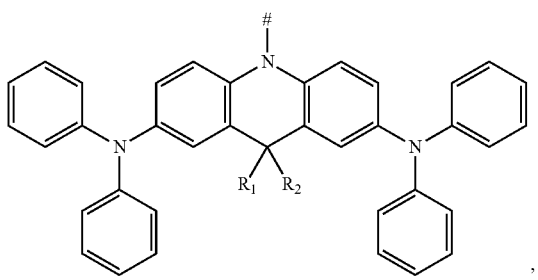

in which $R_1$, $R_2$, $R_3$ and $R_4$ are each independently selected from the group consisting of hydrogen, a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, and a substituted or unsubstituted C4-C40 heteroaryl.

According to an embodiment of the compound of the present disclosure, the electron acceptor A is further selected from the following substituents:

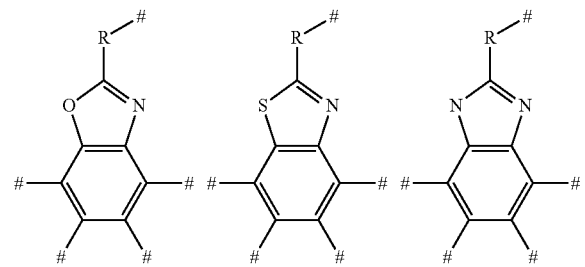

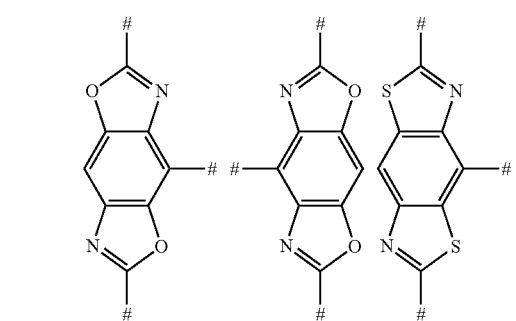

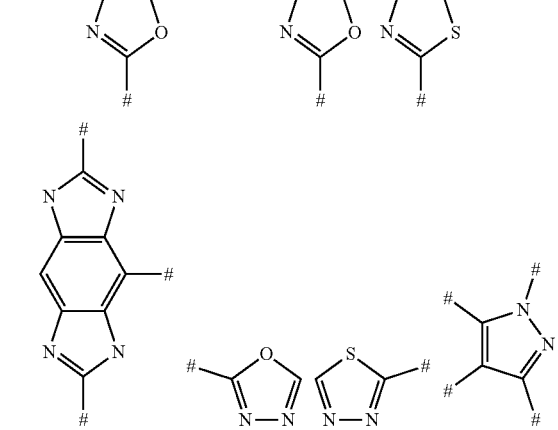

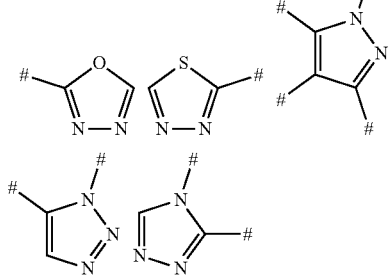

-continued

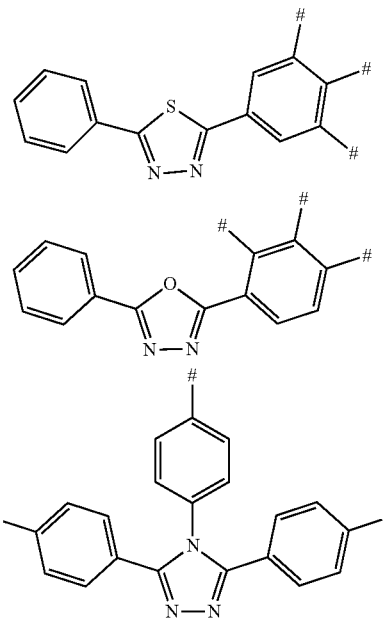

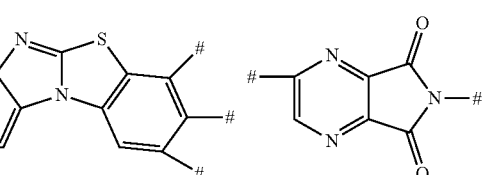

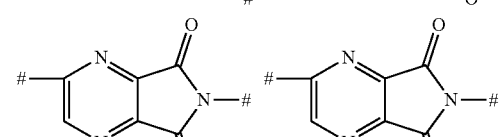

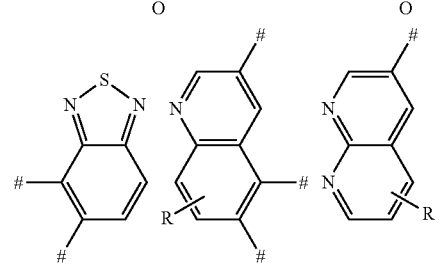

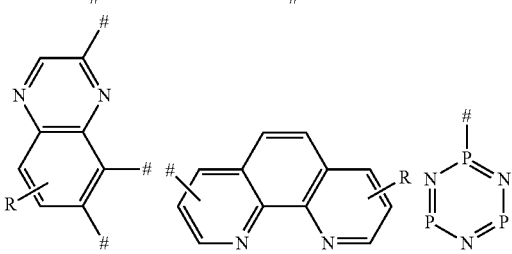

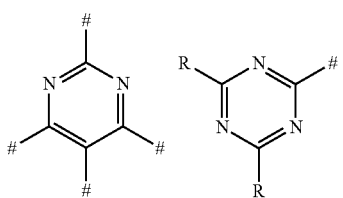

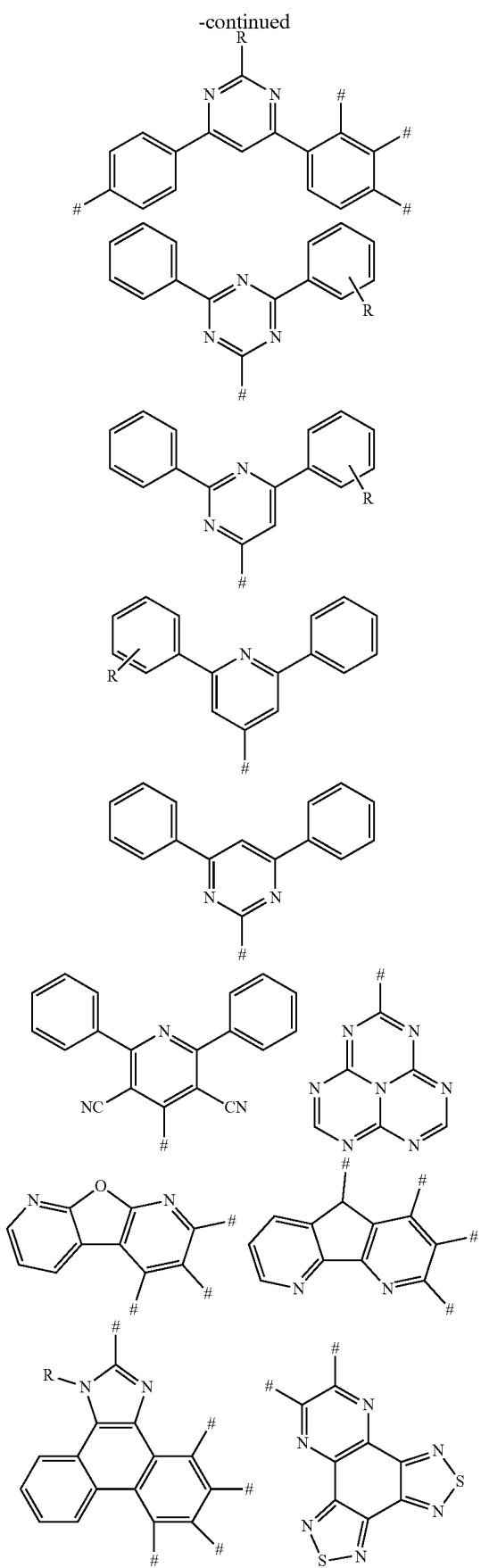
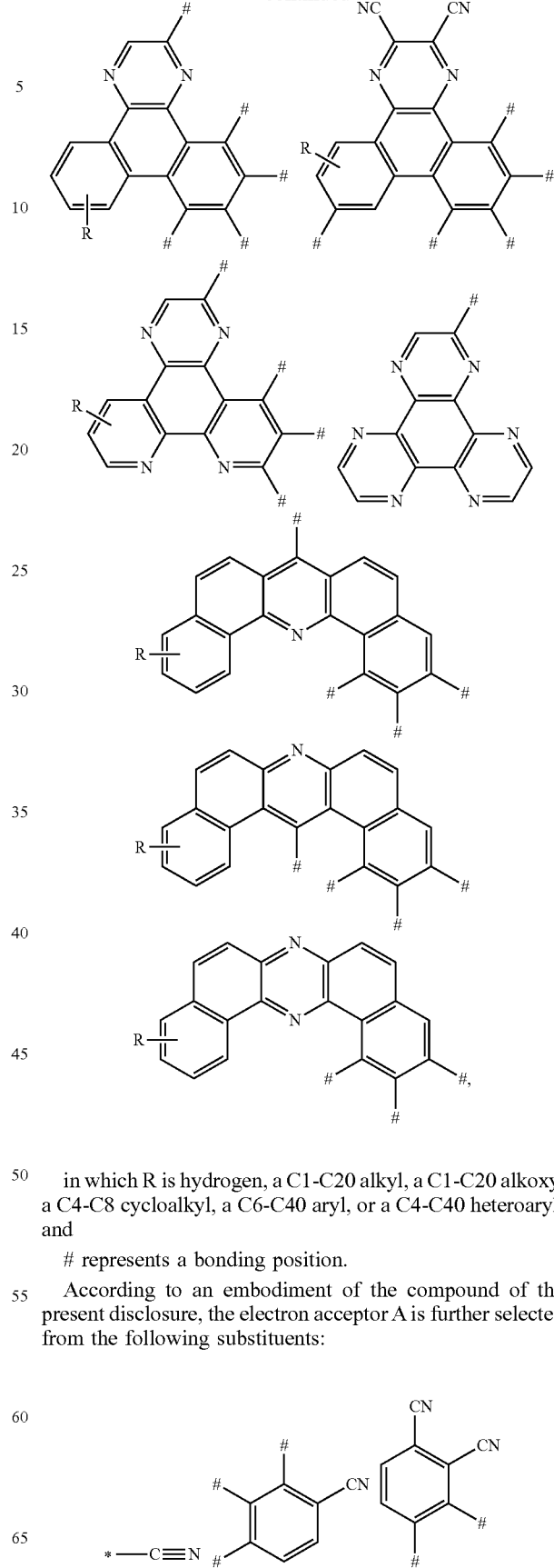
in which R is hydrogen, a C1-C20 alkyl, a C1-C20 alkoxy, a C4-C8 cycloalkyl, a C6-C40 aryl, or a C4-C40 heteroaryl, and
represents a bonding position.
According to an embodiment of the compound of the present disclosure, the electron acceptor A is further selected from the following substituents:
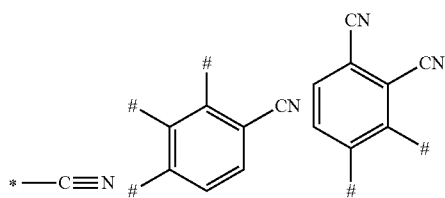

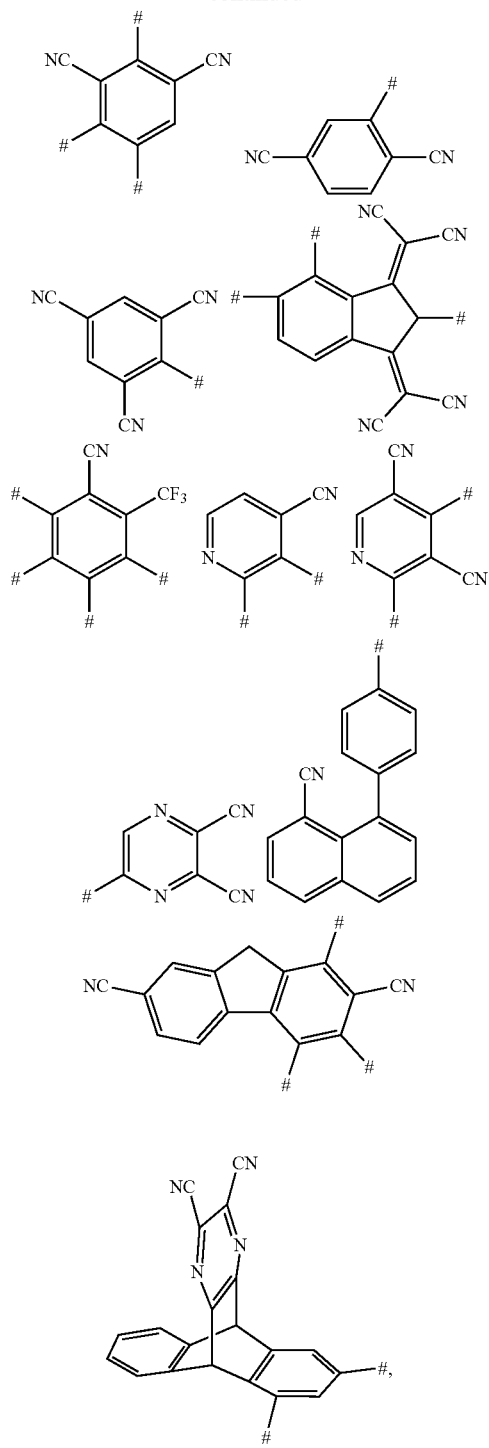

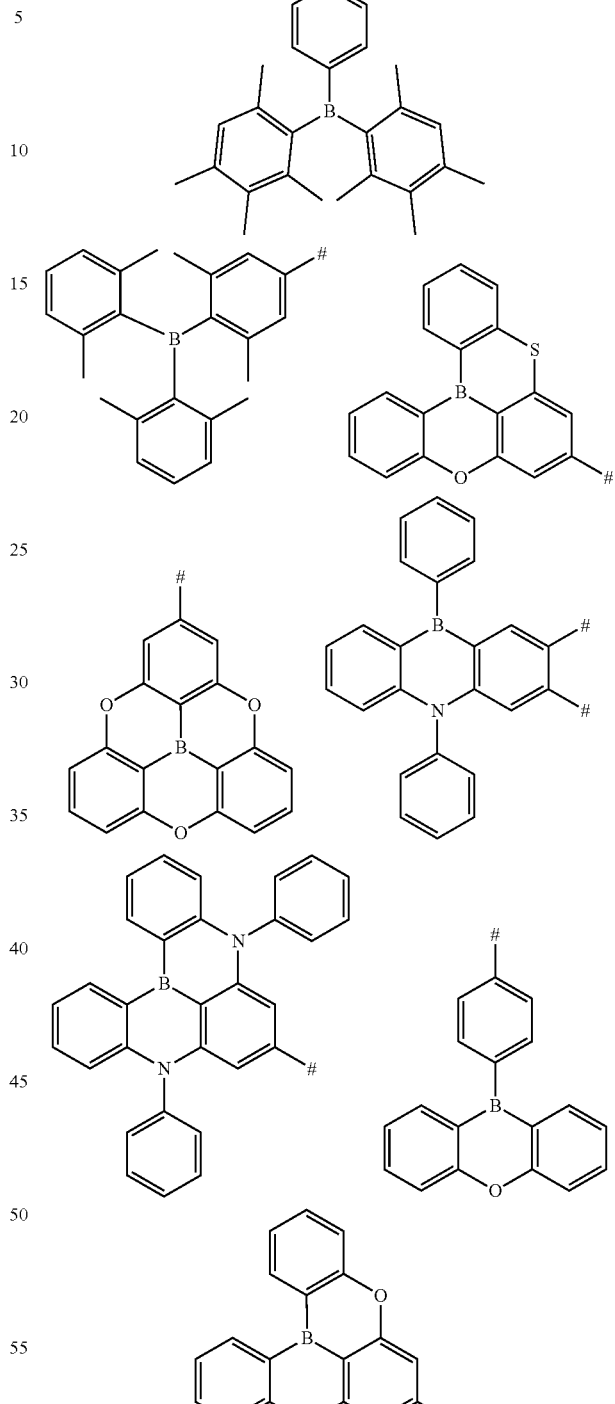

in which # represents a bonding position.

According to an embodiment of the compound of the present disclosure, the electron acceptor A is further selected from the following substituents:

in which # represents a bonding position.

According to an embodiment of the compound of the present disclosure, the electron acceptor A is further selected from the following substituents:

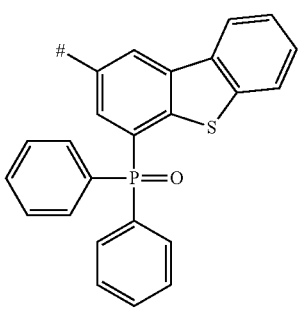
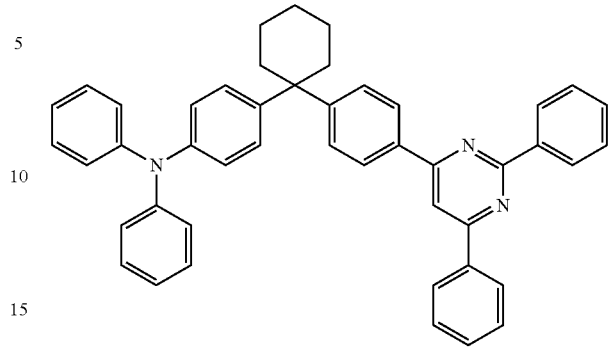
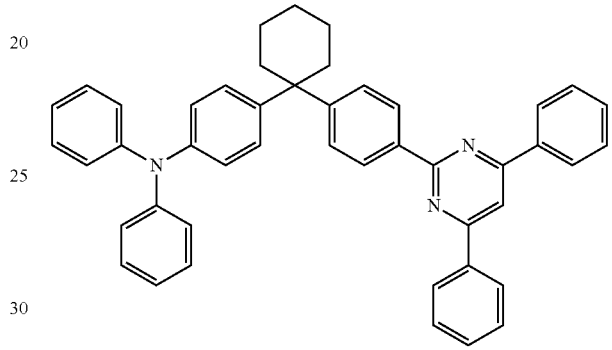
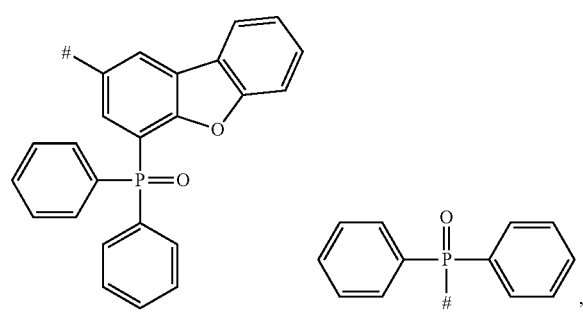
in which # represents a bonding position.
According to an embodiment of the compound of the present disclosure, the compound is further selected from the following compounds:
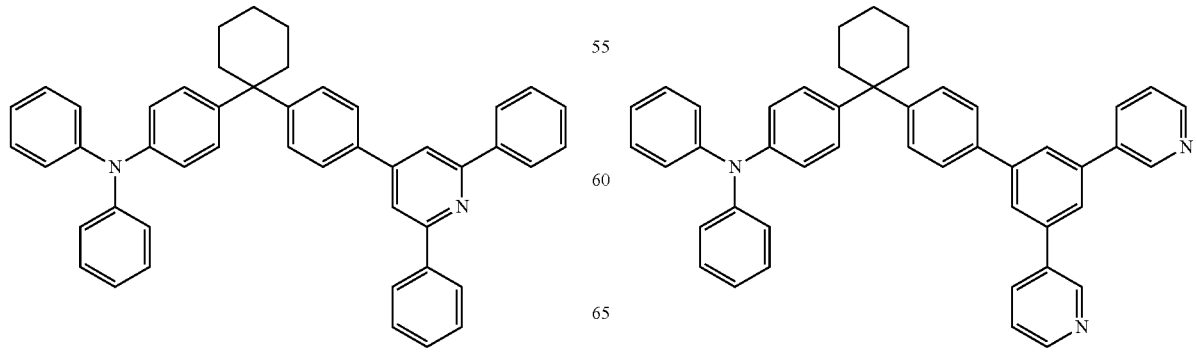

H006
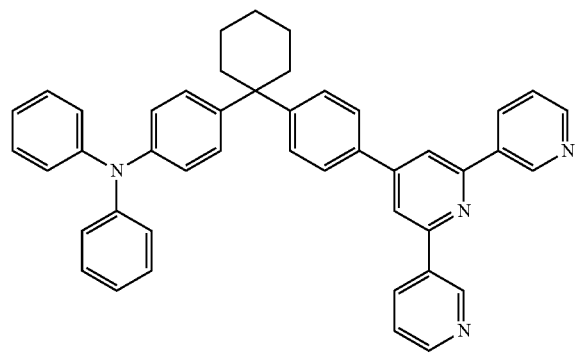
H0010
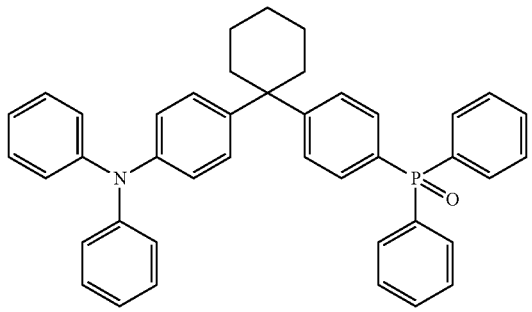
H007
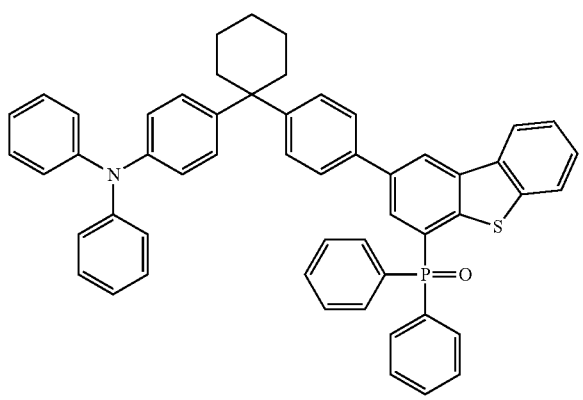
H0011
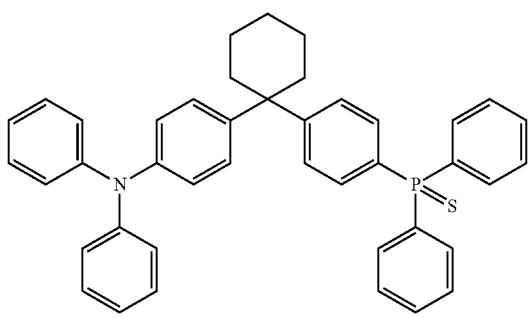
H008
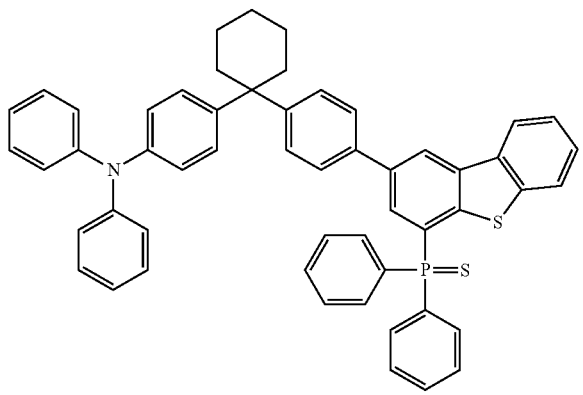
H0012
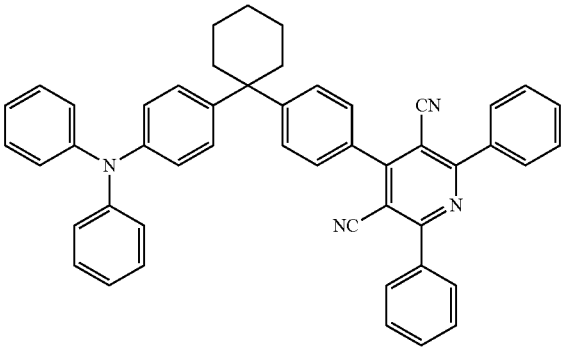
H009
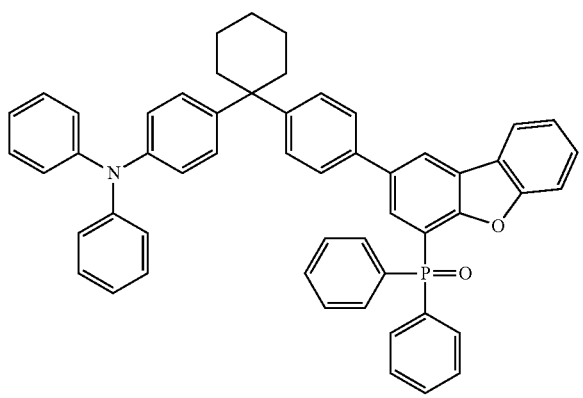
H013
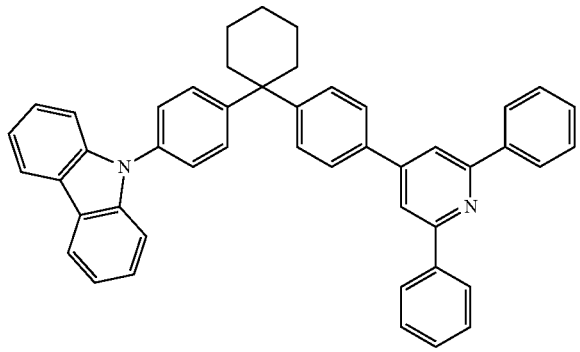

H014
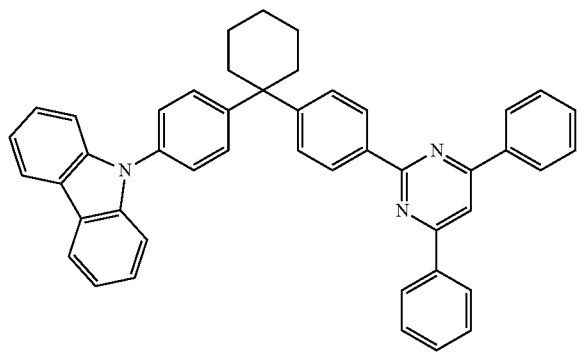
H015
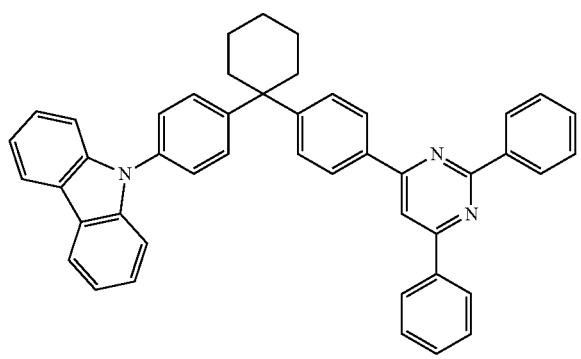
H016
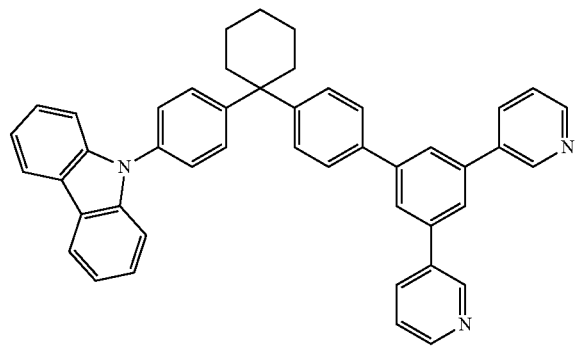
H017
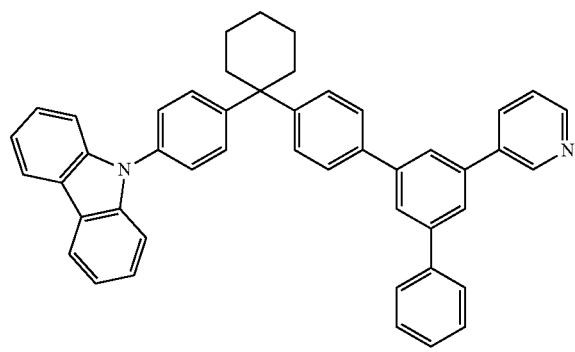
H018
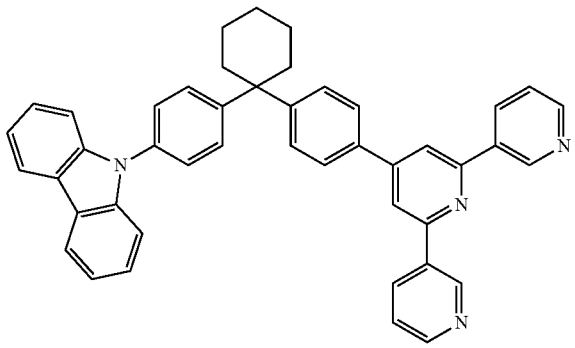
H019
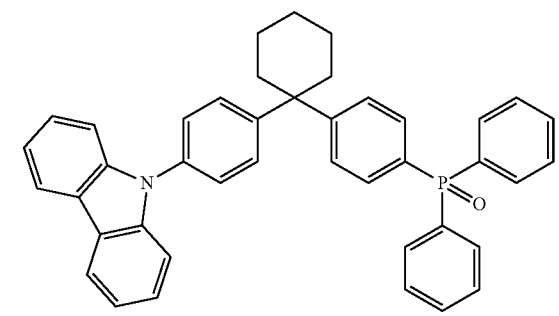
H020
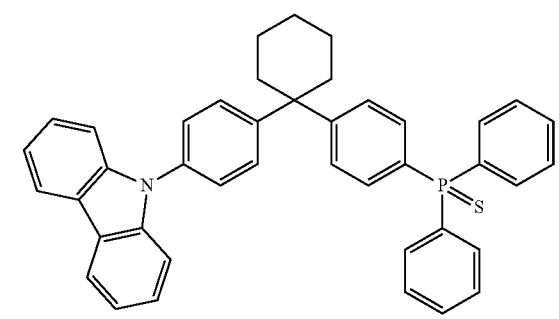
H021
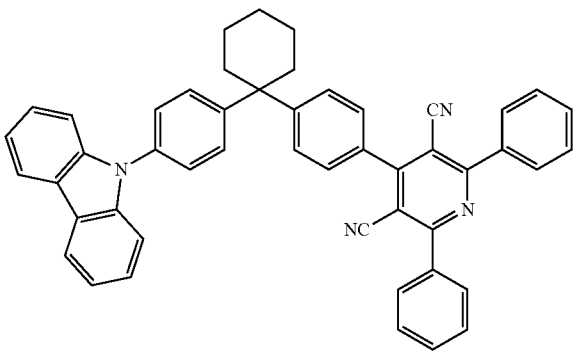

H022
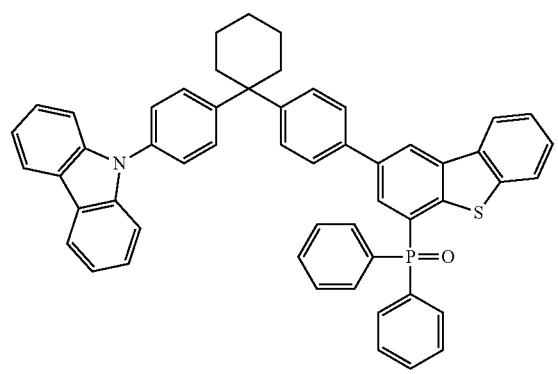
H023
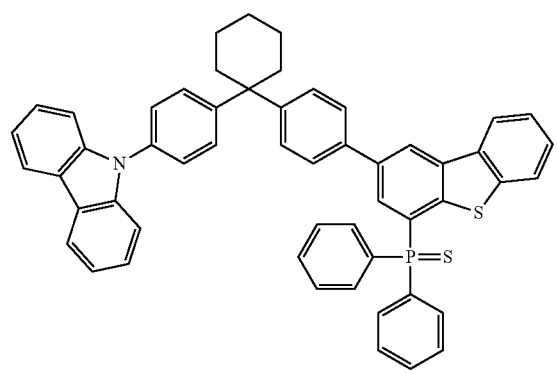
H024
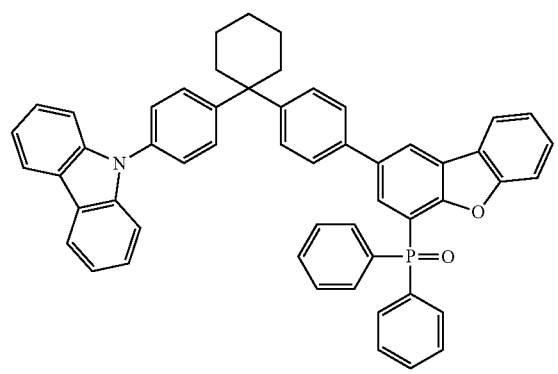
H025
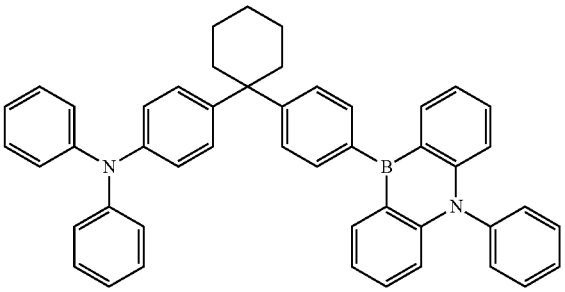
H026
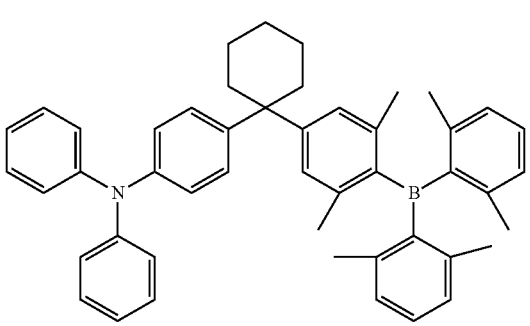
H027
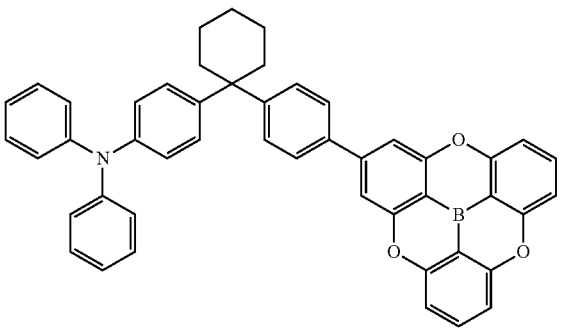
H028
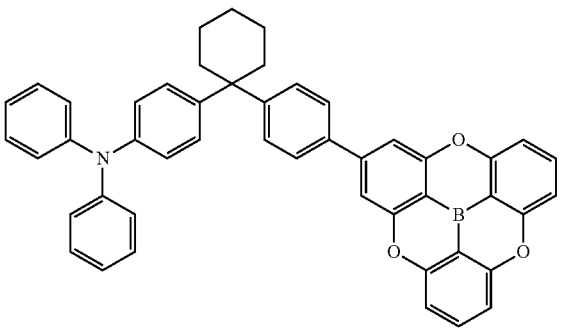
H029
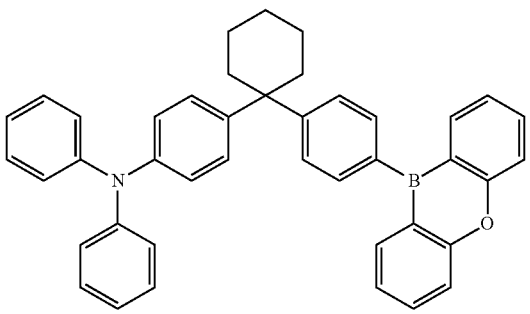

H030
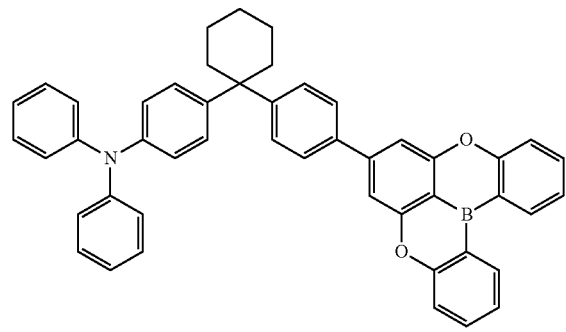
H034
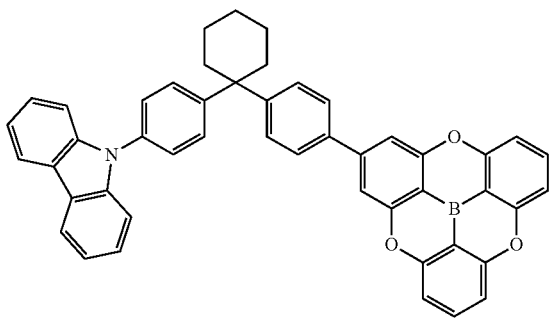
H031
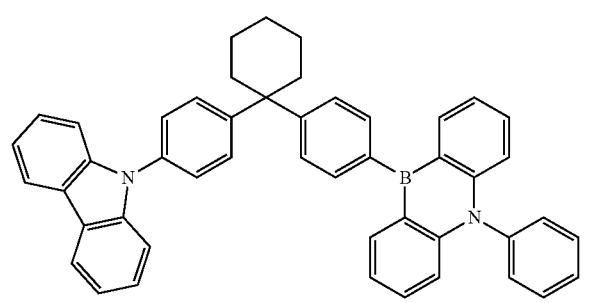
H035
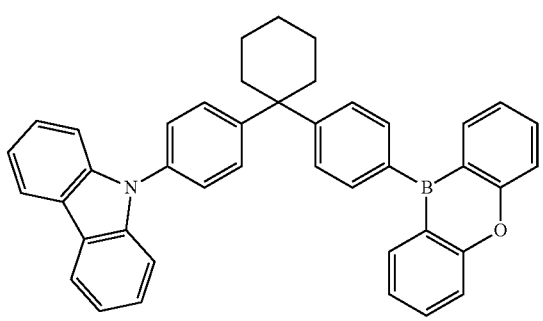
H032
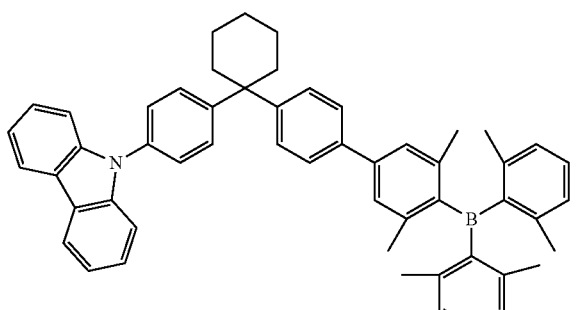
H036
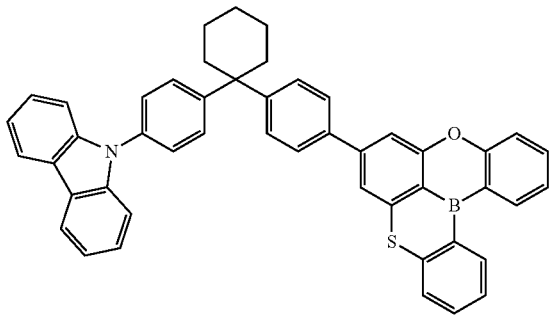
H033
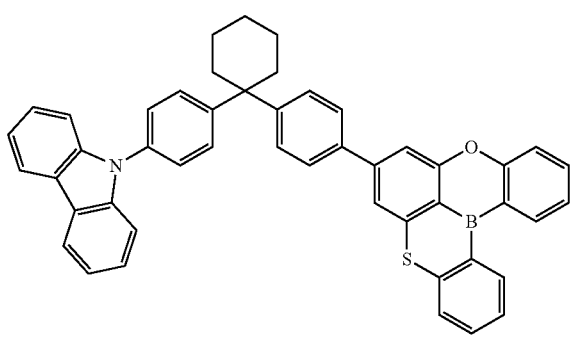
H037
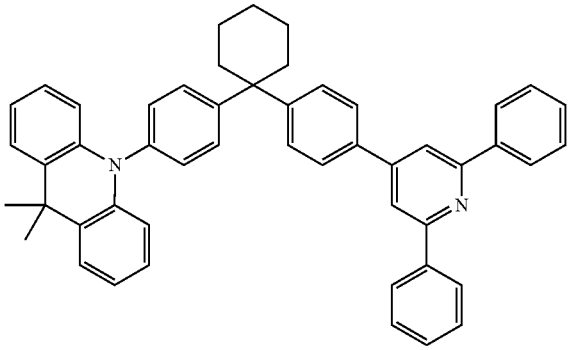

H038
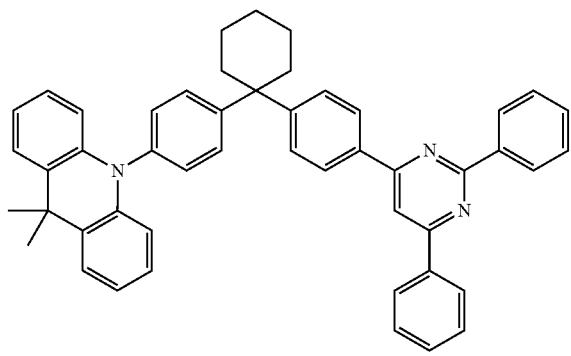
H039
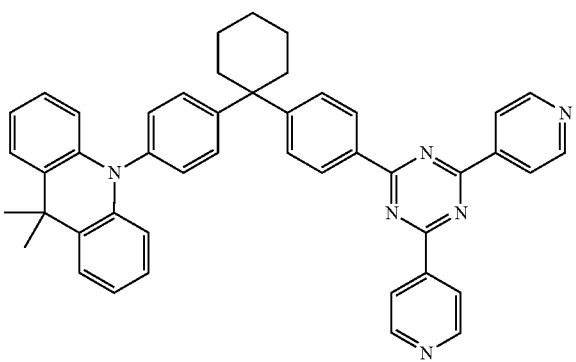
H040
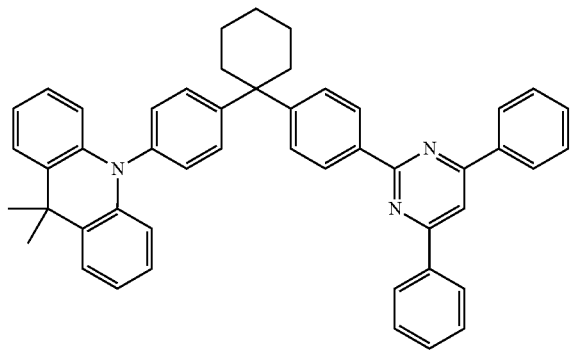
H041
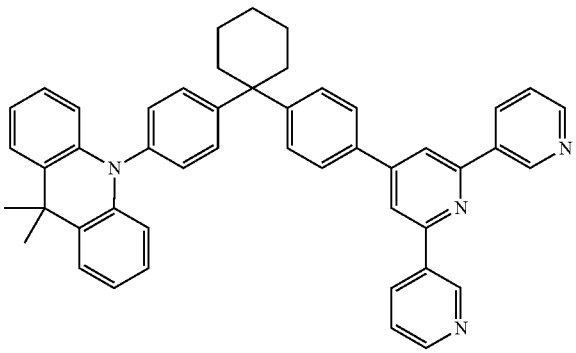
H042
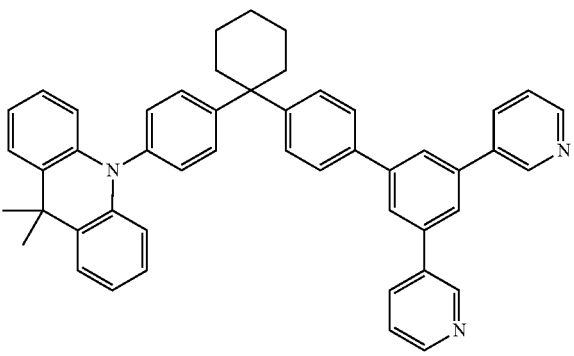
H043
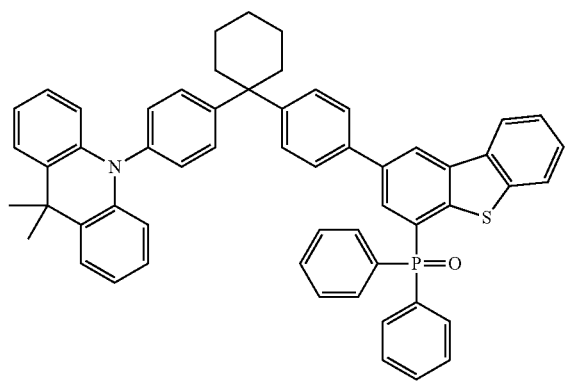
H044
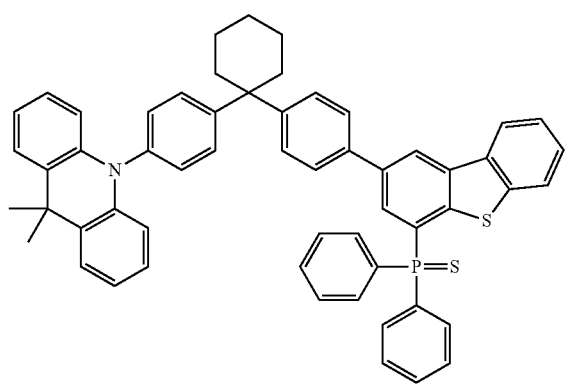
H045
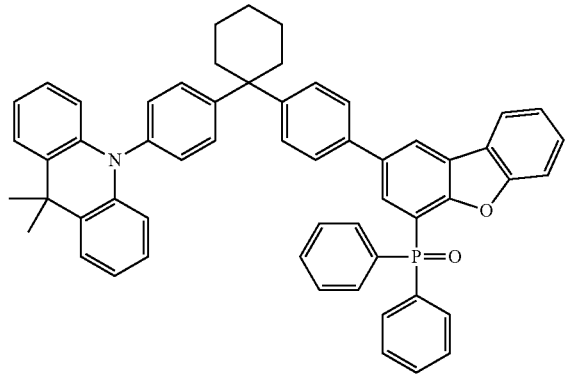

H046
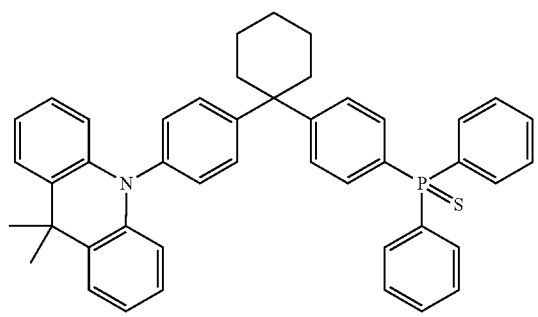
H047
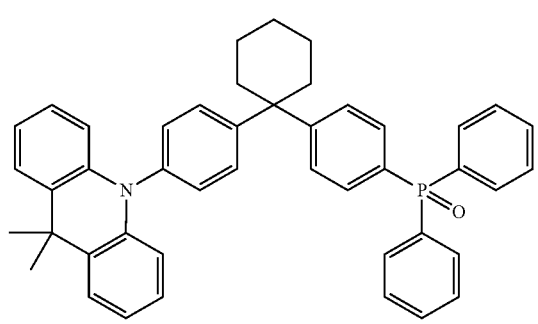
H048
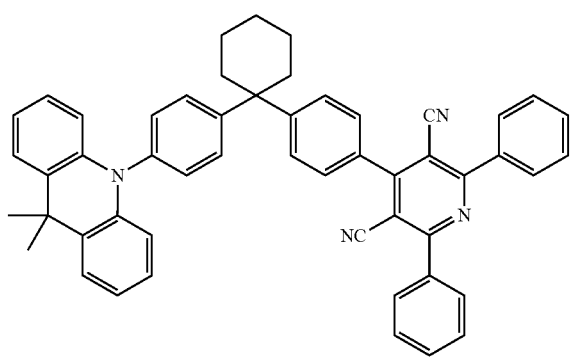
H049
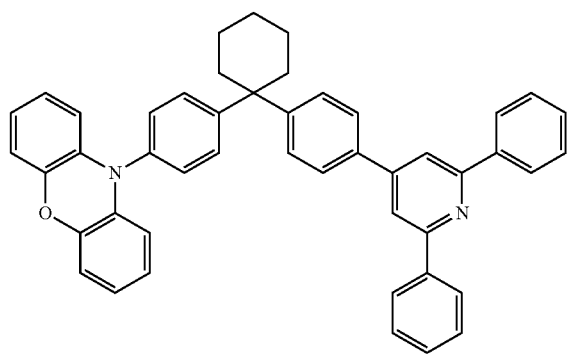
H050
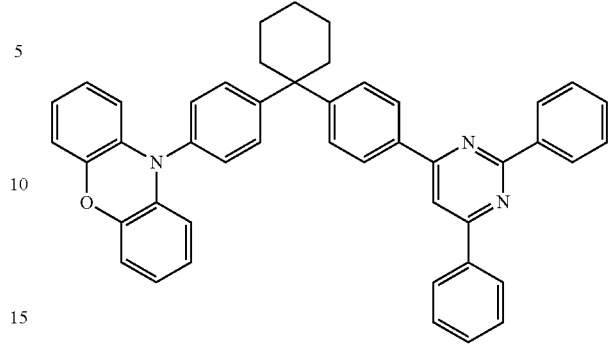
H051
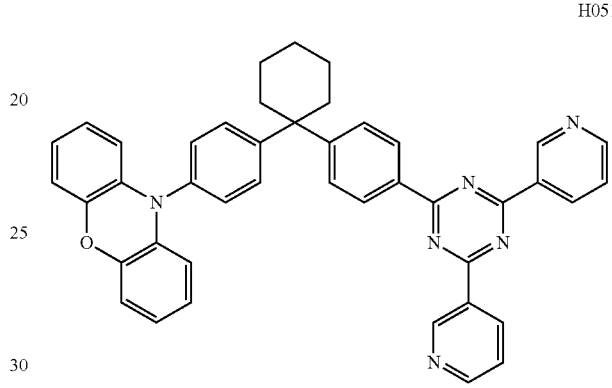
H052
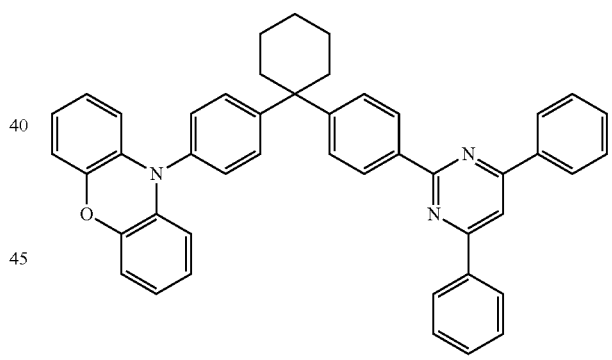
H053
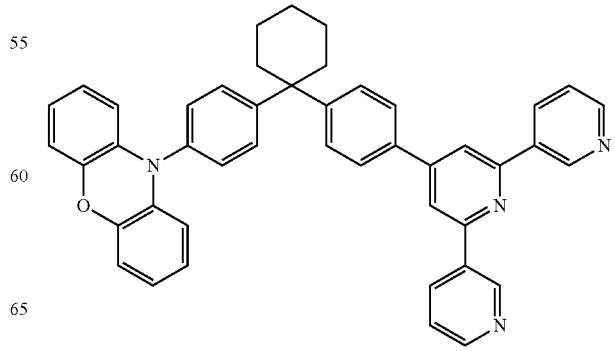

H054
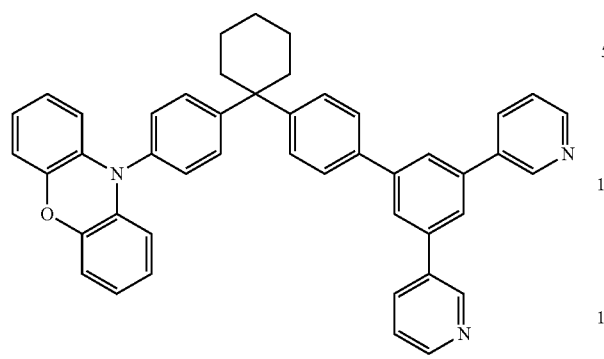
H055
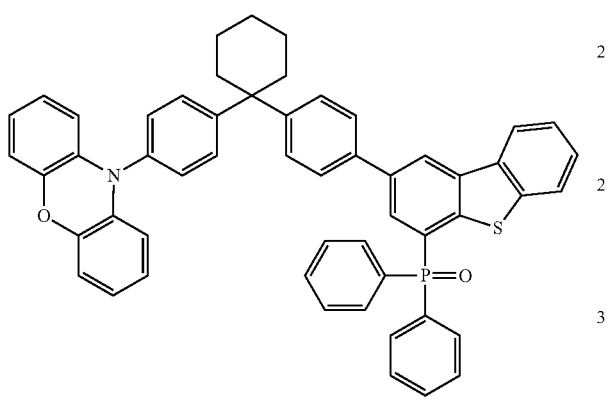
H056
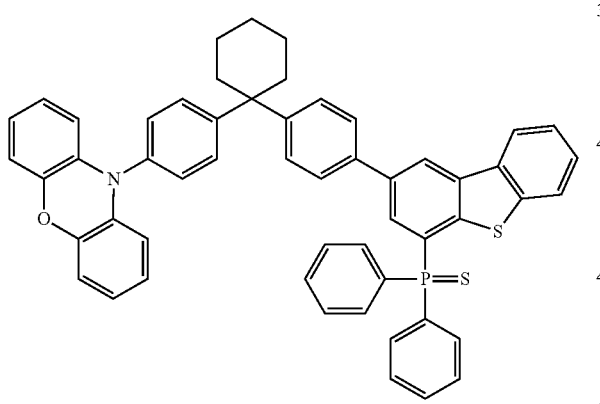
H057
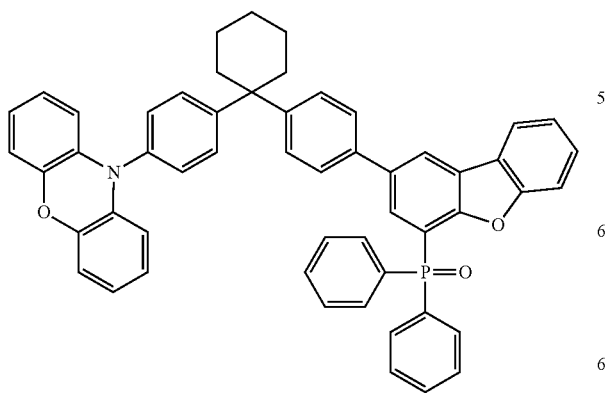
H058
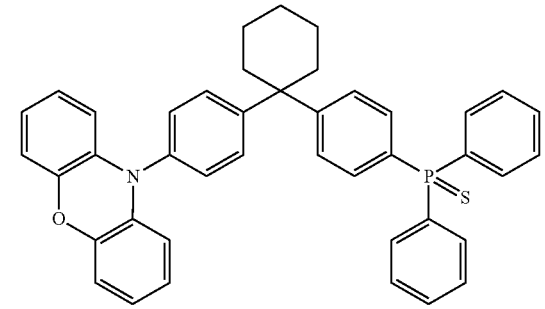
H059
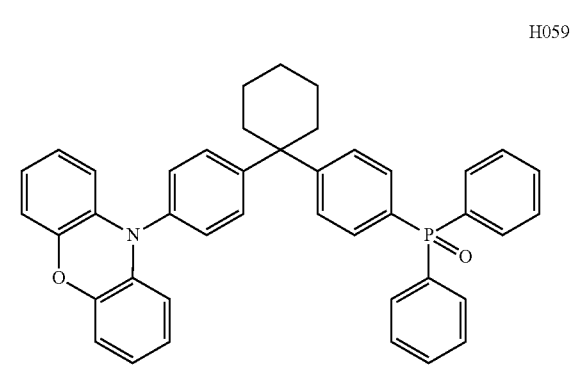
H060
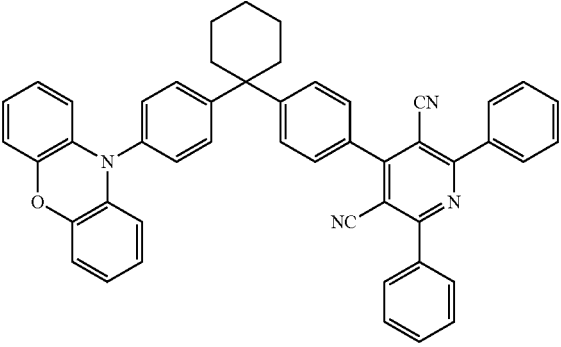
H061
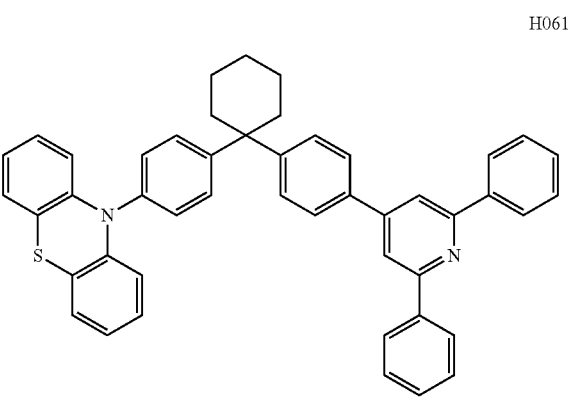

H062
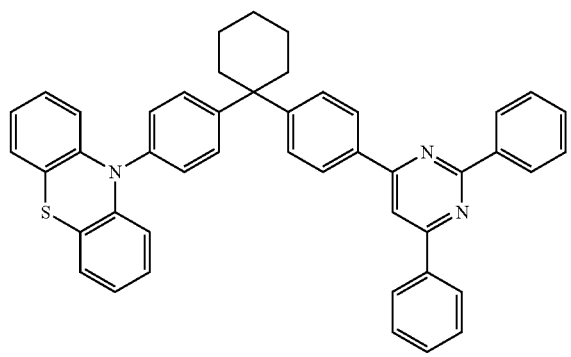
H063
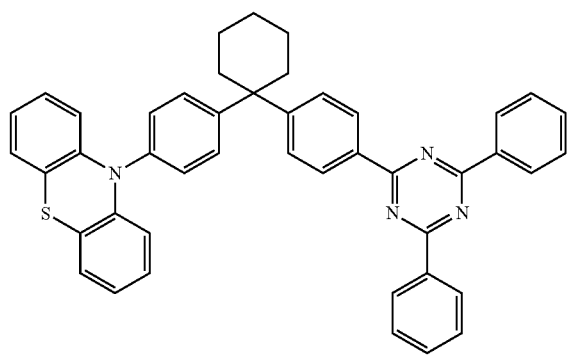
H064
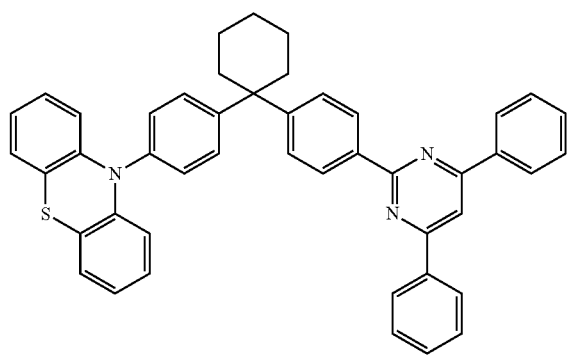
H065
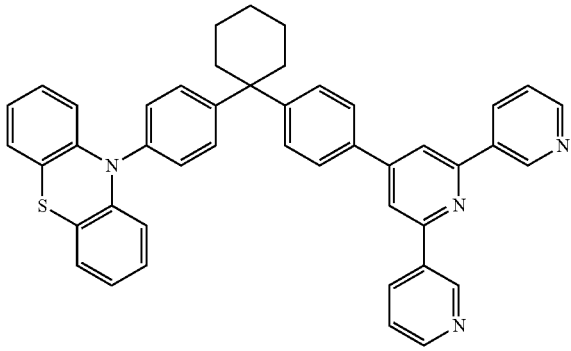
H066
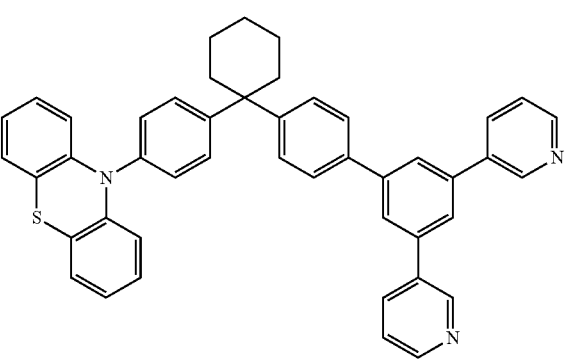
H067
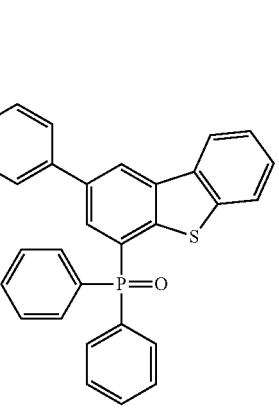
H068
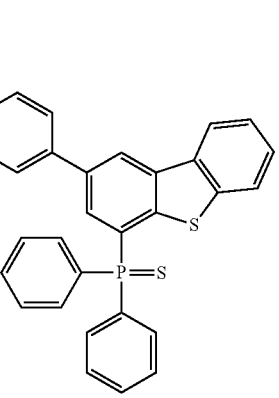
H069
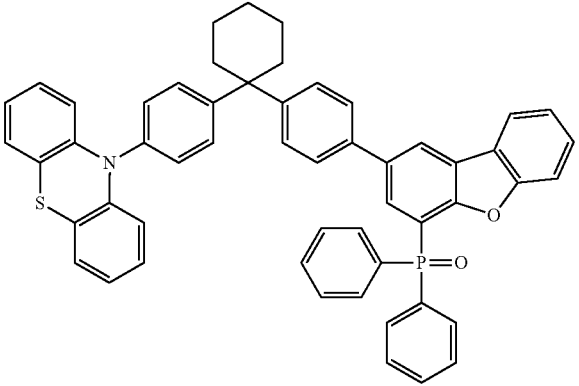

H070
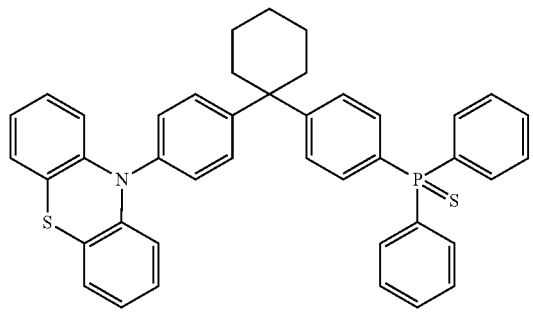
H071
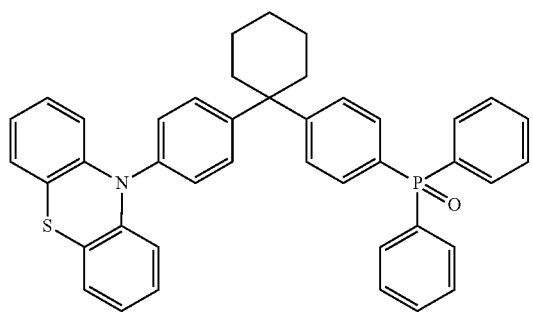
H072
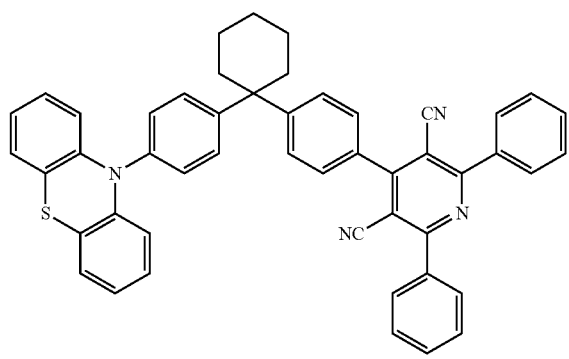
H073
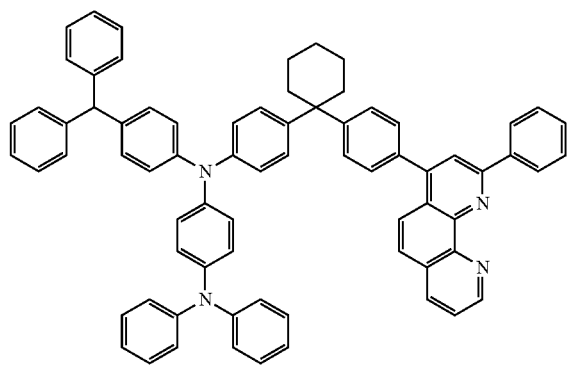
H074
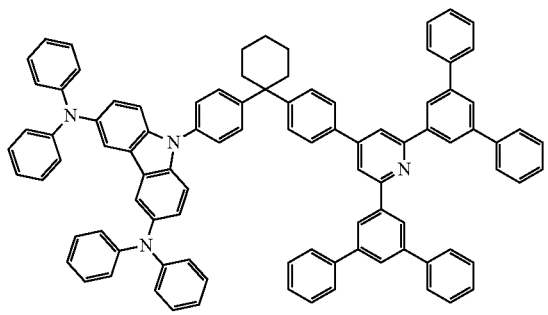
H075
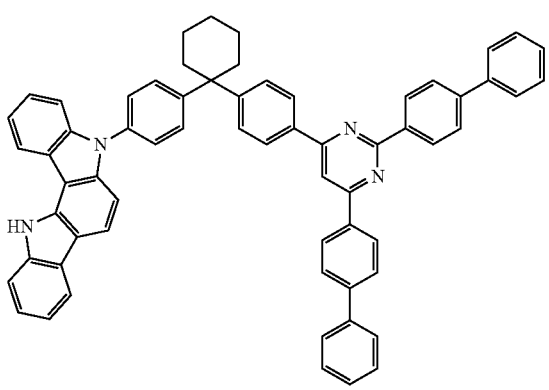
H076
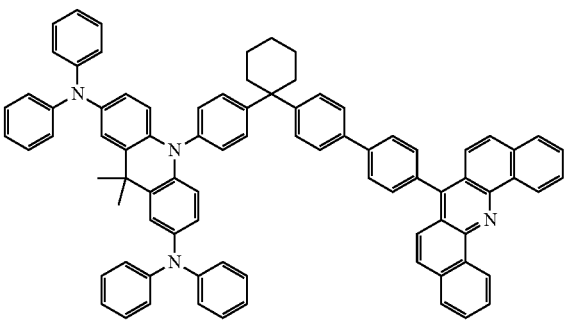
H077
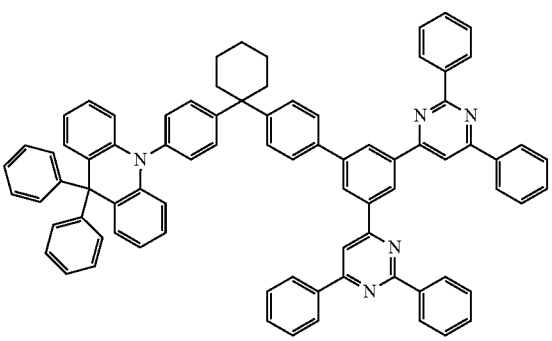

-continued

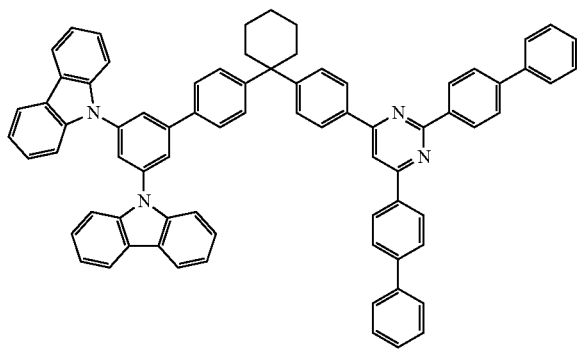
H078

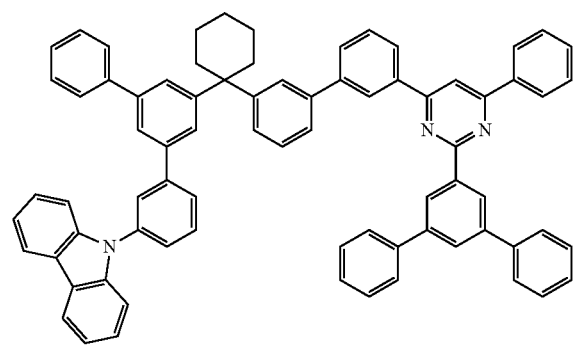
H079

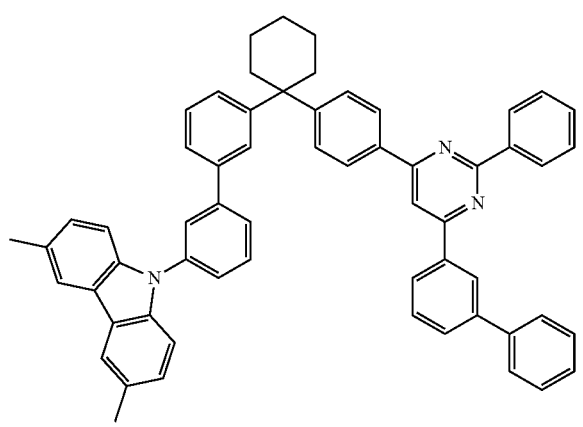
H080

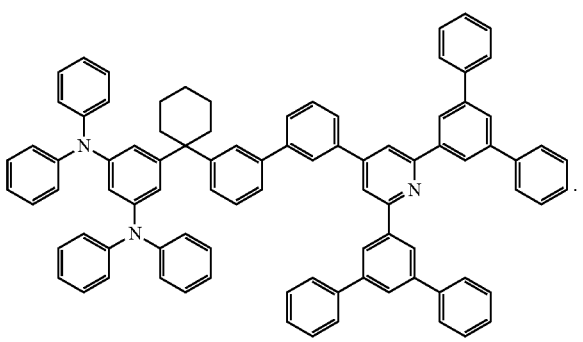
H081

The present disclosure further provides a display panel including an organic light-emitting device. The organic light-emitting device includes an anode, a cathode disposed oppositely to the anode, a light-emitting layer disposed between the anode and the cathode. The light-emitting layer includes a host material and a guest material. The host material is one or more compounds according to the present disclosure.

In the display panel according to the present disclosure, the singlet energy level of the host material is higher than the singlet energy level of the guest material, and the energy difference between the singlet energy level of the host material and the singlet energy level of the guest material is less than 0.8 eV. In addition, the triplet energy level of the host material is higher than the triplet energy level of the guest material, and an energy difference between the triplet energy level of the host material and the triplet energy level of the guest material is less than 0.4 eV.

In the display panel according to the present disclosure, when the host material of the light-emitting layer is a red-light-emitting material, the triplet energy level of the red-light-emitting material has energy greater than or equal to 2.2 eV.

In the display panel according to the present disclosure, when the host material of the light-emitting layer is a green-light-emitting material, the triplet energy level of the green-light-emitting material has energy greater than or equal to 2.5 eV.

In the display panel according to the present disclosure, when the host material of the light-emitting layer is a blue-light-emitting material, the triplet energy level of the blue-light-emitting material has energy greater than or equal to 2.7 eV.

According to an embodiment of the display panel of the present disclosure, the organic light-emitting device further includes one or more of a hole injection layer, a hole transmission layer, an electron blocking layer, a hole blocking layer, an electron transmission layer, and an electron injection layer.

According to an embodiment of the display panel of the present disclosure, the display panel includes an organic light-emitting device. The organic light-emitting device includes an anode, a cathode disposed oppositely to the anode, a capping layer disposed on a side of the cathode facing away from the anode, and an organic layer disposed between the anode and the cathode. The organic layer includes an electron transmission layer, a hole transmission layer, and a light-emitting layer. At least one of the capping layer, the electron transmission layer, the hole transmission layer, and the light-emitting layer is made of the compound according to the present disclosure.

In the display panel provided by the present disclosure, the anode of the organic light-emitting device can be made of a material selected from a group consisting of metals, such as copper, gold, silver, iron, chromium, nickel, manganese, palladium, platinum, etc., and alloys thereof; metal oxides, such as indium oxide, zinc oxide, indium tin oxide (ITO), indium zinc oxide (IZO), and the like; and conductive polymers, such as polyaniline, polypyrrole, poly(3-methylthiophene) and the like. In addition to the above-mentioned anode materials and the combinations thereof that are conductive to injecting holes, the anode also can be made of other suitable material known in the related art.

In the display panel provided by the present disclosure, the cathode of the organic light-emitting device can be made of a material selected from metals, such as aluminum, magnesium, silver, indium, tin, titanium, etc., and alloys thereof; and multi-layered metal materials, such as LiF/Al, $LiO_2$/Al, $BaF_2$/Al, and the like. In addition to the above-mentioned cathode materials and the combinations thereof that are conductive to injecting electrons, the cathode also can be made of other suitable material known in the related art.

According to an embodiment of the present disclosure, the organic light-emitting device of the display panel can be manufactured by forming an anode on a transparent or opaque smooth substrate, forming a thin organic layer on the anode, and further forming a cathode on the thin organic layer. The thin organic layer can be formed by a known film forming method such as vapor deposition, sputtering, spin coating, dipping, ion plating, and the like. Finally, an organic optical capping layer CPL (covering layer) was formed on the cathode. The optical capping layer CPL can be made of the compound according to the present disclosure. The optical capping layer CPL can be prepared by vapor deposition or solution processing method. The solution processing method include ink jet printing, spin coating, knife coating, screen printing, roll-to-roll printing, and the like.

The synthesis of several exemplary compounds is described below.

EXAMPLE 1

Synthesis of Compound H004

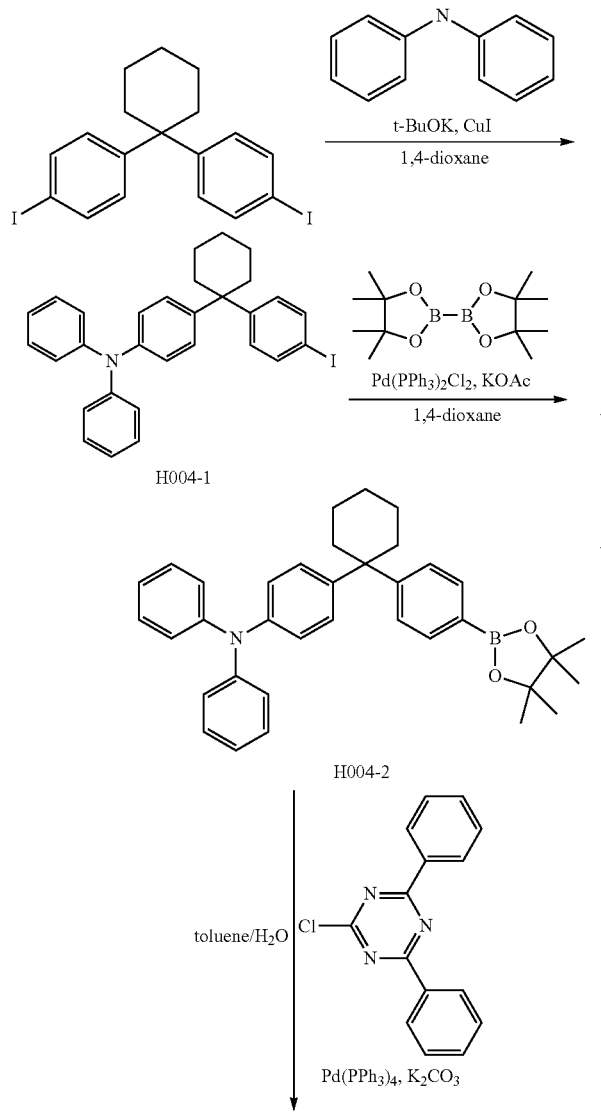

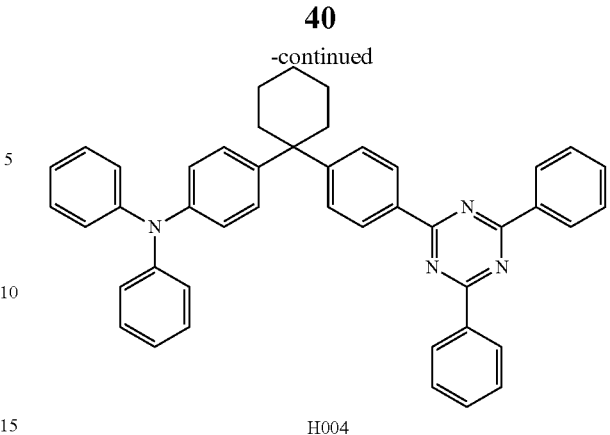

1,1-bis(4-iodophenyl)cyclohexane (15 mmol), copper iodide (15 mmol), potassium tert-butoxide (65 mmol), 1,2-diamino cyclohexane (12 mmol) and diarylamine (25 mmol) were added to dry 1,4-dioxane (400 mL) in a round bottom flask (250 mL), and the mixture was refluxed under nitrogen atmosphere for 48 hours. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H004-1.

The intermediate product H004-1 (15 mmol) and potassium acetate (40 mmol) were mixed with dry 1,4-dioxane (60 mL), Pd(PPh$_3$)$_2$Cl$_2$ (0.4 mmol) and bis(pinacolato)diboron (25 mmol) in a round bottom flask (250 mL). The mixture was stirred at 90° C. for 48 hours under nitrogen atmosphere. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H004-2.

The intermediate product H004-2 (10 mmol), 2-chloro-4,6-diphenyl-triazine (12 mmol) and Pd(PPh$_3$)$_4$ (0.3 mmol) were added to a mixture of toluene (30 mL)/ethanol (20 mL) and an aqueous solution (10 mL) of potassium carbonate (12 mmol) in a round bottom flask (250 mL). The obtained mixture was refluxed for 12 hours under nitrogen atmosphere, added to water after being cooled to room temperature, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield a final product H004.

Elemental analysis of the Compound H004 (molecular formula C$_{45}$H$_{38}$N$_4$): theoretical values: C, 85.14; H, 6.03; N, 8.83; tested values: C, 85.14; H, 6.02; N, 8.84. Liquid chromatography-mass spectrometry ESI-MS (m/z) (M+): theoretical value: 634.31; tested value: 634.51.

EXAMPLE 2

Synthesis of Compound H022

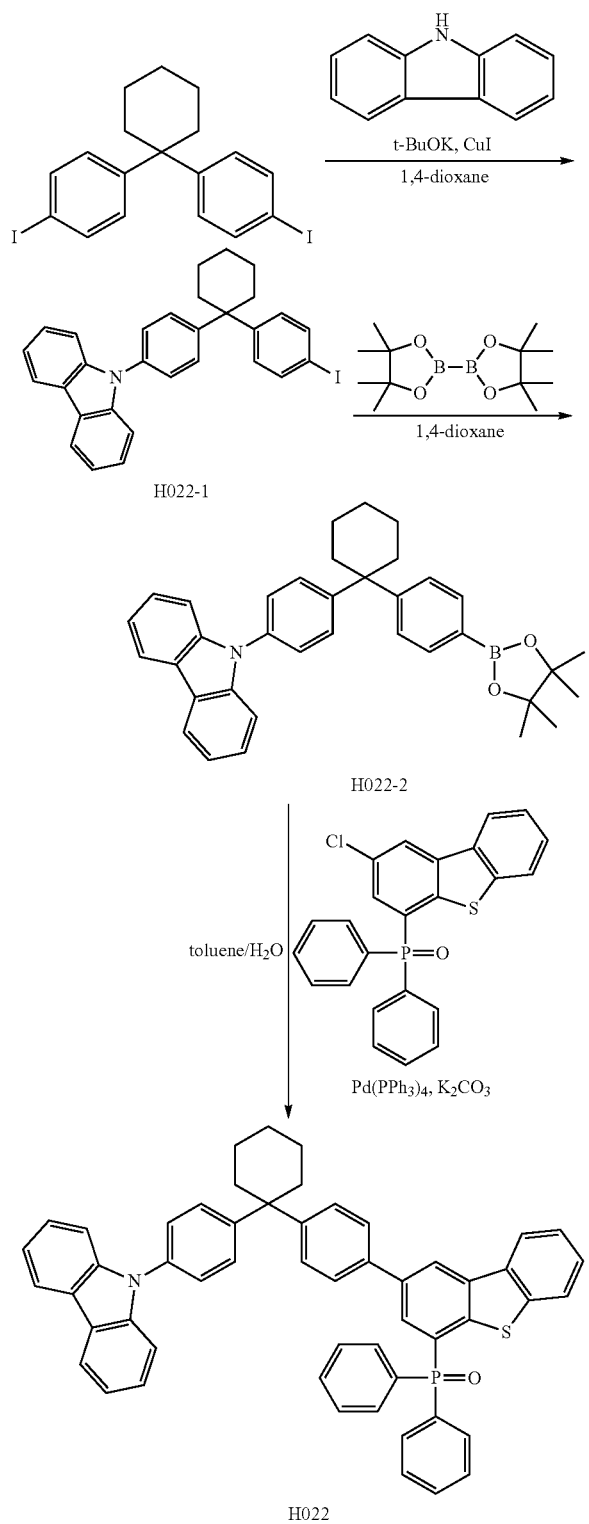

1,1-bis(4-iodophenyl)cyclohexane (15 mmol), copper iodide (15 mmol), potassium tert-butoxide (65 mmol), 1,2-diamino cyclohexane (12 mmol) and 9-carbazole (25 mmol) were added to dry 1,4-dioxane (400 mL) in a round bottom flask (250 mL), and the mixture was refluxed under nitrogen atmosphere for 48 hours. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H022-1.

The intermediate product H022-1 (15 mmol) and potassium acetate (40 mmol) were mixed with dry 1,4-dioxane (60 mL), Pd(PPh$_3$)$_2$Cl$_2$ (0.4 mmol) and bis(pinacolato)diboron (25 mmol) in a round bottom flask (250 mL). The mixture was stirred at 90° C. for 48 hours under nitrogen atmosphere. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H022-2.

The intermediate product H022-2 (10 mmol), 2-chloro-4-(diphenylphosphono)-dibenzothiophene (12 mmol) and Pd(PPh$_3$)$_4$ (0.3 mmol) were added to a mixture of toluene (30 mL)/ethanol (20 mL) and an aqueous solution (10 mL) of potassium carbonate (12 mmol) in the round bottom flask (250 mL). The obtained mixture was refluxed for 12 hours under nitrogen atmosphere, added to water after being cooled to room temperature, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield a final product H022.

Elemental analysis of the Compound H022 (molecular formula C$_{54}$H$_{42}$NOPS): theoretical values: C, 82.73; H, 5.40; N, 1.79; O, 2.04; P, 3.95; S, 4.09; tested values: C, 82.73; H, 5.41; N, 1.78; O, 2.04; P, 3.95; S, 4.09. Liquid chromatography-mass spectrometry ESI-MS (m/z) (M+): theoretical value: 783.27; tested value: 783.86.

EXAMPLE 3

Synthesis of Compound H048

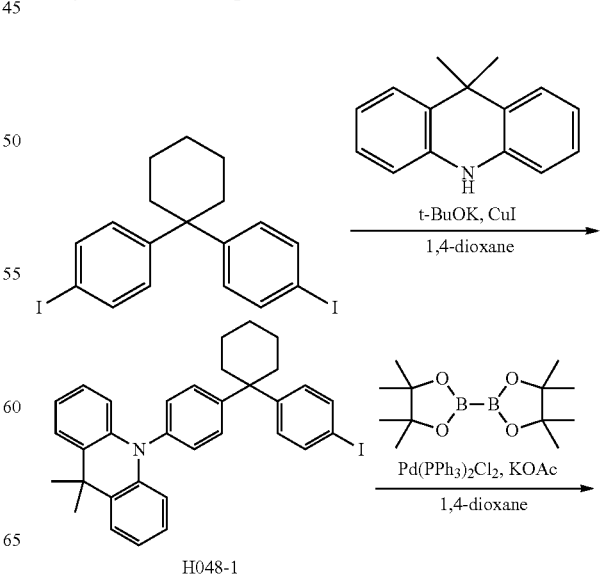

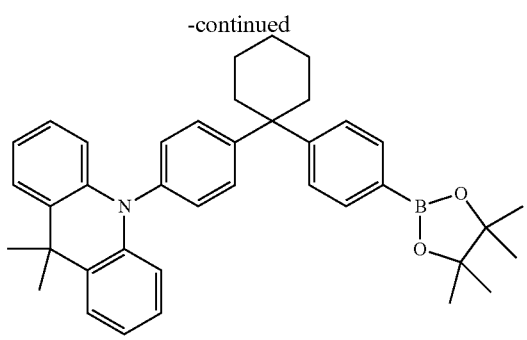

H048-2

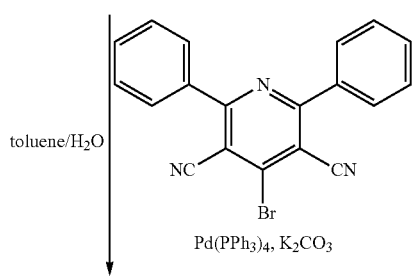

Pd(PPh₃)₄, K₂CO₃ toluene/H₂O

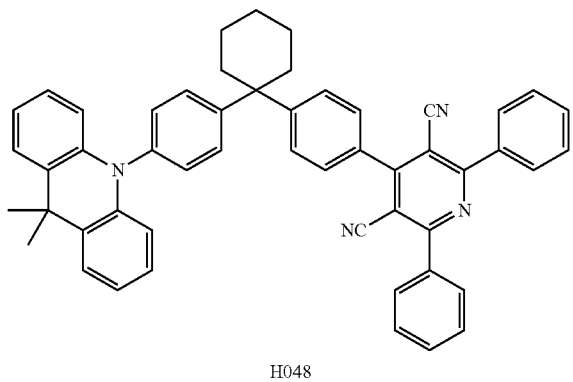

H048

1,1-bis(4-iodophenyl)cyclohexane (15 mmol), copper iodide (15 mmol), potassium tert-butoxide (65 mmol), 1,2-diamino cyclohexane (12 mmol) and 9,9-dimethyl acridine (25 mmol) were added to dry 1,4-dioxane (400 mL) in a round bottom flask (250 mL), and the mixture was refluxed under nitrogen atmosphere for 48 hours. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H048-1.

The intermediate product H048-1 (15 mmol) and potassium acetate (40 mmol) were mixed with dry 1,4-dioxane (60 mL), Pd(PPh₃)₂Cl₂ (0.4 mmol) and bis(pinacolato)diboron (25 mmol) in the round bottom flask (250 mL). The mixture was stirred at 90° C. for 48 hours under nitrogen atmosphere. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H048-2.

The intermediate product H048-2 (10 mmol), 4-bromo-2,6-diphenylpyridine-3,5-dicarbonitrile (12 mmol) and Pd(PPh₃)₄ (0.3 mmol) were added to a mixture of toluene (30 mL)/ethanol (20 mL) and an aqueous solution (10 mL) of potassium carbonate (12 mmol) in a round bottom flask (250 mL). The obtained mixture was refluxed for 12 hours under nitrogen atmosphere, added to water after being cooled to room temperature, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield a final product H048.

Elemental analysis of the Compound H048 (molecular formula $C_{52}H_{42}N_4$): theoretical values: C, 86.39; H, 5.86; N, 7.75; tested values: C, 86.39; H, 5.87; N, 7.74. Liquid chromatography-mass spectrometry ESI-MS (m/z) (M+): theoretical value: 722.34; tested values: 722.67.

EXAMPLE 4

Synthesis of Compound H077

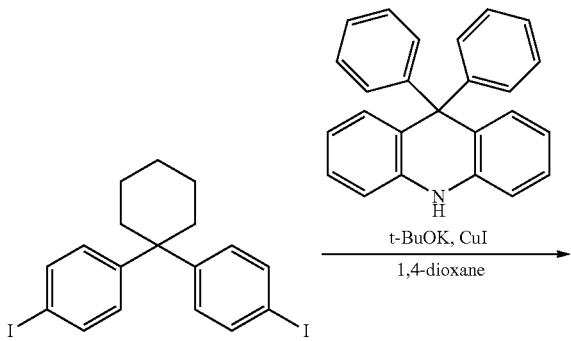

t-BuOK, CuI
1,4-dioxane

-continued
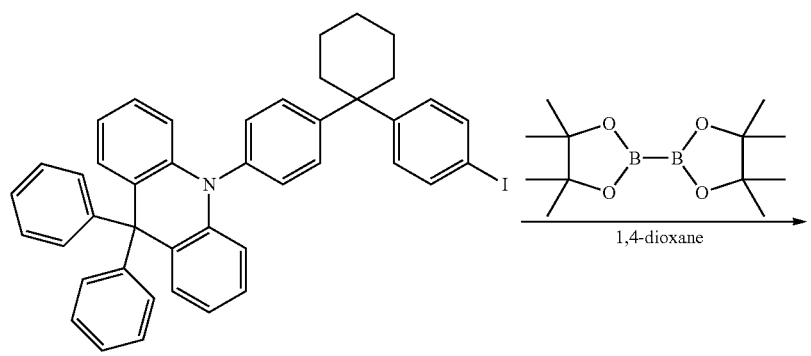
H077-1
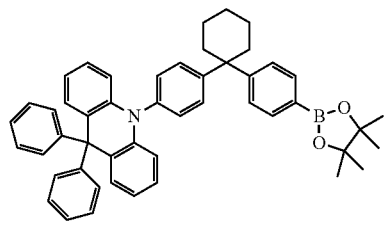
H077-2
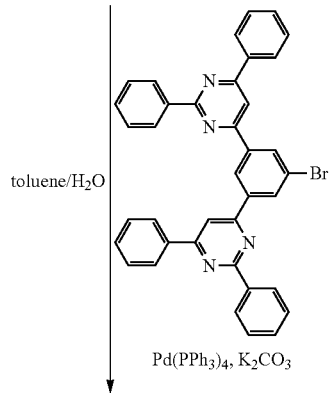
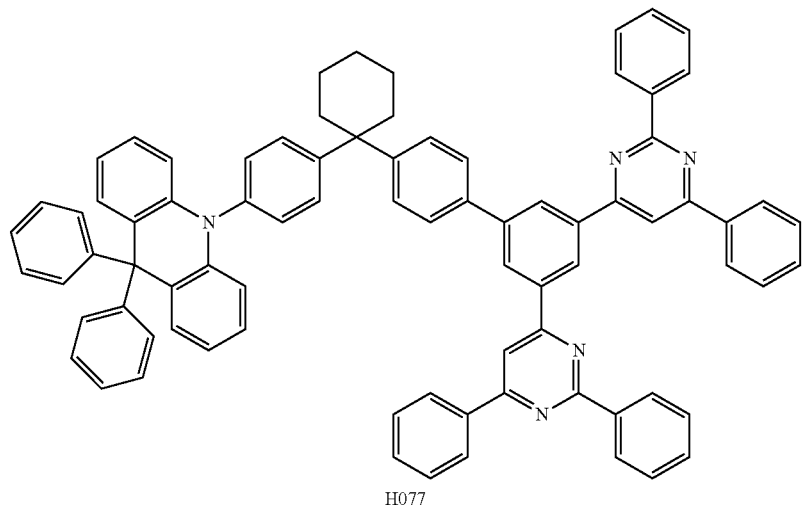
H077

1,1-bis(4-iodophenyl)cyclohexane (15 mmol), copper iodide (15 mmol), potassium tert-butoxide (65 mmol), 1,2-diamino cyclohexane (12 mmol) and 9,9-diphenyl-9,10-dihydroacridine (25 mmol) were added to dry 1,4-dioxane (400 mL) in a round bottom flask (250 mL), and the mixture was refluxed under nitrogen atmosphere for 48 hours. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H077-1.

The intermediate product H077-1 (15 mmol) and potassium acetate (40 mmol) were mixed with dry 1,4-dioxane (60 mL), Pd(PPh$_3$)$_2$Cl$_2$ (0.4 mmol) and bis(pinacolato)diboron (25 mmol) in the round bottom flask (250 mL). The mixture was stirred at 90° C. for 48 hours under nitrogen atmosphere. The obtained intermediate was cooled to room temperature, added to water, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield an intermediate product H077-2.

The intermediate product H077-2 (10 mmol), 1-bromo-3,5-bis(2,6-diphenylpyrimidine)benzene (12 mmol) and Pd(PPh$_3$)$_4$ (0.3 mmol) were added to a mixture of toluene (30 mL)/ethanol (20 mL) and an aqueous solution (10 mL) of potassium carbonate (12 mmol) in a round bottom flask (250 mL). The obtained mixture was refluxed for 12 hours under nitrogen atmosphere, added to water after being cooled to room temperature, and then filtered through a diatomite pad. The filtrate was extracted with dichloromethane, then washed with water and dried over anhydrous magnesium sulfate. A crude product was obtained after filtration and evaporation, and then purified by silica gel column chromatography to yield a final product H077.

Elemental analysis of the Compound H077 (molecular formula $C_{81}H_{61}N_5$): theoretical values: C, 88.09; H, 5.57; N, 6.34; tested values: C, 88.09; H, 5.58; N, 6.33. Liquid chromatography-mass spectrometry ESI-MS (m/z) (M+): theoretical value: 1103.49; tested values: 1103.84.

TABLE 1

Energy level of compounds

| Compound | HOMO (eV) | LUMO (eV) | Eg (eV) | $E_T$ (eV) |
|---|---|---|---|---|
| H004 | −5.423 | −2.327 | 3.096 | 2.9147 |
| H022 | −5.459 | −2.291 | 3.168 | 2.9983 |
| H048 | −5.416 | −2.315 | 3.101 | 2.9208 |
| H077 | −5.503 | −2.372 | 3.131 | 2.9314 |

It can be seen from the above Table 1 that the Compounds H004, H022, H048 and H077, as the host material, show appropriate HOMO and LUMO energy levels and extremely high triplet energy $E_T$ (>2.9 eV). Thus, these compounds are suitable to be applied as the host materials of red light (at least $E_T$>2.2 eV), green light (at least $E_T$>2.5 eV), and blue light (at least $E_T$>2.7 eV), and can effectively achieve the energy transfer between the host material and the guest material without the risk of reverse charge transfer.

EXAMPLE 5

Figure 2:
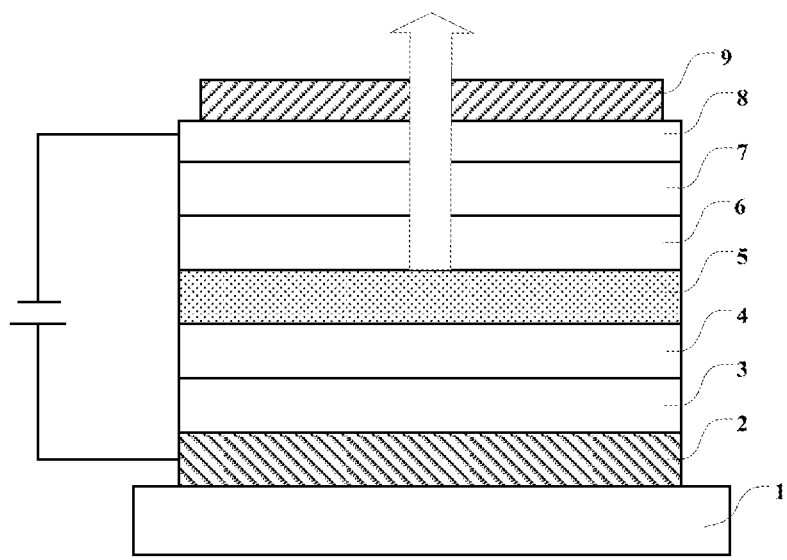
FIG. 2 is a structural schematic diagram of an OLED device according to an embodiment of the present disclosure.

This example provides an organic light-emitting device. As shown in FIG. 2, the organic light-emitting device includes a glass substrate 1, an ITO anode 2, a first hole transmission layer 3, a second hole transmission layer 4, a light-emitting layer 5, a first electron transmission layer 6, a second electron transmission layer 7, a cathode 8 (magnesium silver electrode with a mass ratio of magnesium to silver of 9:1) and a capping layer (CPL) 9. The ITO anode 2 has a thickness of 15 nm, the first hole transmission layer 3 has a thickness of 10 nm, and the second hole transmission layer 4 has a thickness of 95 nm, the light-emitting layer 5 has a thickness of 30 nm, the first electron transmission layer 6 has a thickness of 35 nm, the second electron transmission layer 7 has a thickness of 5 nm, the magnesium silver electrode 8 has a thickness of 15 nm, and the capping layer (CPL) 9 has a thickness of 100 nm.

The organic light-emitting device of this example was manufactured according to the following steps:

(1) The glass substrate 1 was cut into a size of 50 mm×50 mm×0.7 mm, then subjected to ultrasonic treatment in isopropyl alcohol and deionized water for 30 minutes, respectively, and then exposed to ozone for about 10 minutes for cleaning. The obtained glass substrate 1 with the ITO anode 2 was placed on a vacuum deposition equipment.

(2) A material HAT-CN was vacuum evaporated onto the ITO anode 2 to form the first hole transmission layer 3 having a thickness of 10 nm.

(3) A second hole transmission layer material TAPC was vapor evaporated onto the first hole transmission layer 3 to form the second hole transmission layer 4 having a thickness of 95 nm.

(4) The light-emitting layer 5 having a thickness of 30 nm was co-deposited on the hole transmission layer 4, where in the light-emitting layer 5 Compound H004 was used as the host material, and Ir(ppy)$_3$ was used as the dopeing material with a mass ratio of Compound H004 to Ir(ppy)$_3$ of 19:1.

(5) A material BPen was vacuum evaporated onto the light-emitting layer 5 to form the first electron transmission layer 6 having a thickness of 30 nm.

(6) A material Alq3 was vacuum evaporated onto the first electron transmission layer 6 to form the second electron transmission layer 7 having a thickness of 5 nm.

(7) The magnesium silver electrode having a thickness of 15 nm, as the cathode 8, was formed on the second electron transmission layer 7 by vacuum evaporating magnesium and silver with a mass ratio of mamesium to silver of 9:1.

(8) A hole type material CBP having a high refraction index was vacuum evaporated onto the cathode 8 to form a cathode covering layer (capping layer or CPL) 9 having a thickness of 100 nm.

The compounds and the structures thereof involved in the present embodiment are shown as follow.

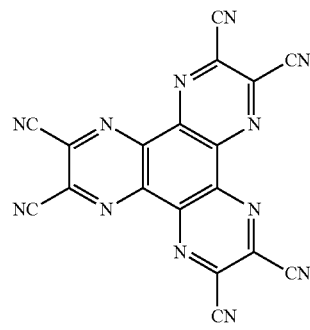

HAT-CN

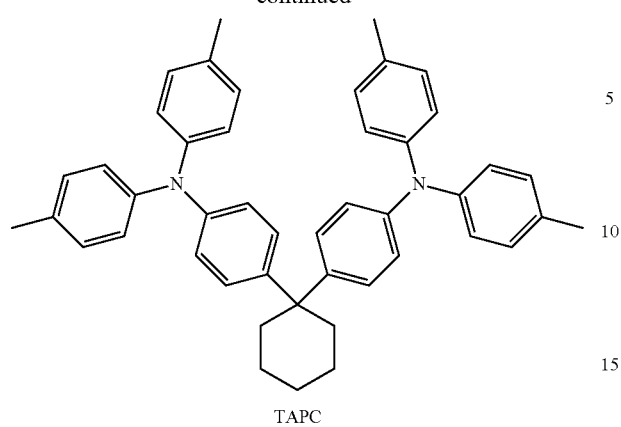

TAPC

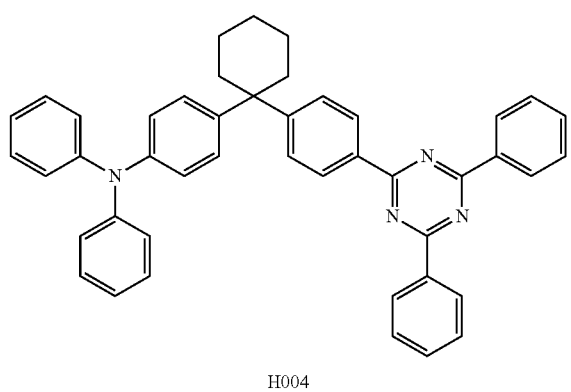

H004

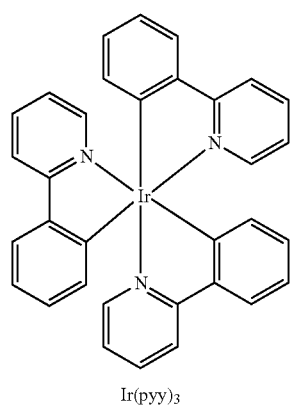

Ir(pyy)₃

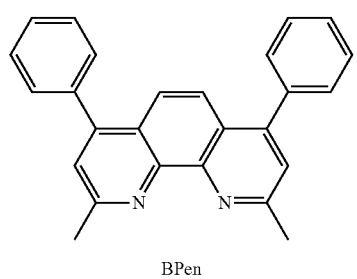

BPen

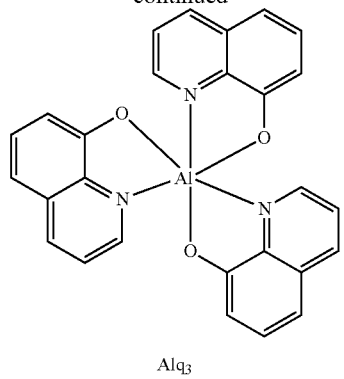

Alq₃

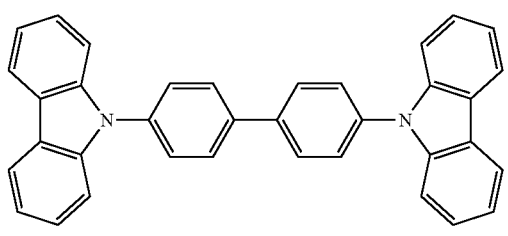

CBP

EXAMPLE 6

In Example 6, the device was manufactured according to the steps described in Example 5, and the material of each layer was the same except the Compound H022 was used as the host material.

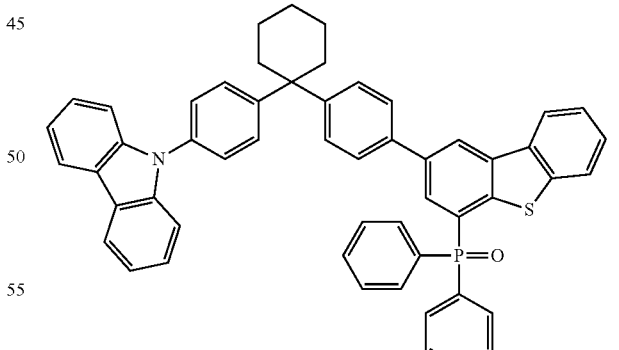

H022

EXAMPLE 7

In Example 7, the device was manufactured according to the steps described in Example 5, and the material of each layer was the same except the Compound H048 was used as the host material.

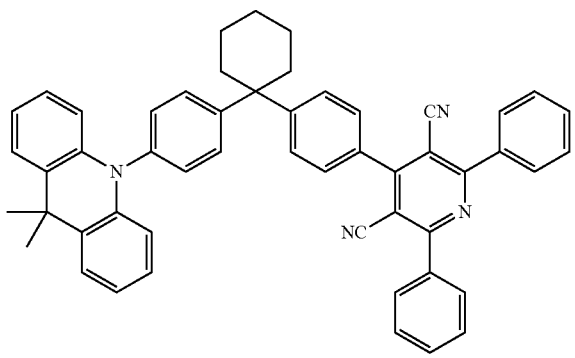

H048

EXAMPLE 8

In Example 8, the device was manufactured according to the steps described in Example 5, and the material of each layer was the same except the Compound H077 was used as the host material.

COMPARATIVE EXAMPLE 1

In Comparative Example 1, the device was manufactured according to the steps described in Example 5, the material of each layer was the same except the host material is CzTRZ.

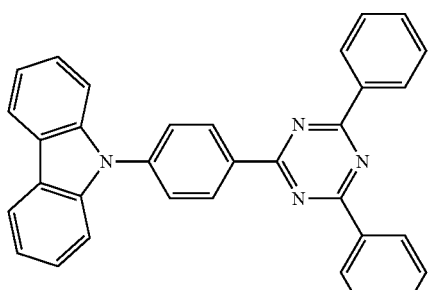

CzTRZ

TABLE 2

Measurement results of luminescence performance of devices

| No. | host material | driving voltage (V) | EQE/% | CE (cd/A) | LT95 (at 50 mA/cm$^2$) |
|---|---|---|---|---|---|
| Example 5 | H004 | 3.79 | 30.9% | 126.5 | 79.4 |
| Example 6 | H022 | 3.85 | 31.5% | 125.9 | 80.1 |
| Example 7 | H048 | 3.82 | 29.7% | 127.4 | 78.8 |
| Example 8 | H077 | 3.77 | 31.2% | 126.0 | 82.9 |
| Comparative Example 1 | CzTRZ | 4.10 | 24.2% | 103.2 | 67.2 |

It can be seen from Table 2 that the driving voltages of the light-emitting devices adopting the compounds of the present disclosure are about 8.5% lower than the driving voltage of the device of the comparative example 1, so that power consumption of the device can be effectively reduced. Compared with the device of the comparative example 1, the luminous efficiency of the light-emitting devices using the compounds of the present disclosure as the host material is improved by about 10%-25%, thereby effectively improving the brightness of the devices; and the service life of the light-emitting devices adopting the compounds of the present disclosure as the host material is also prolonged by about 18% or more.

In another example, the present disclosure provides a display panel including the above-mentioned organic light-emitting device.

In still another example, the present disclosure provides a display apparatus including the above-mentioned display panel.

Figure 3:
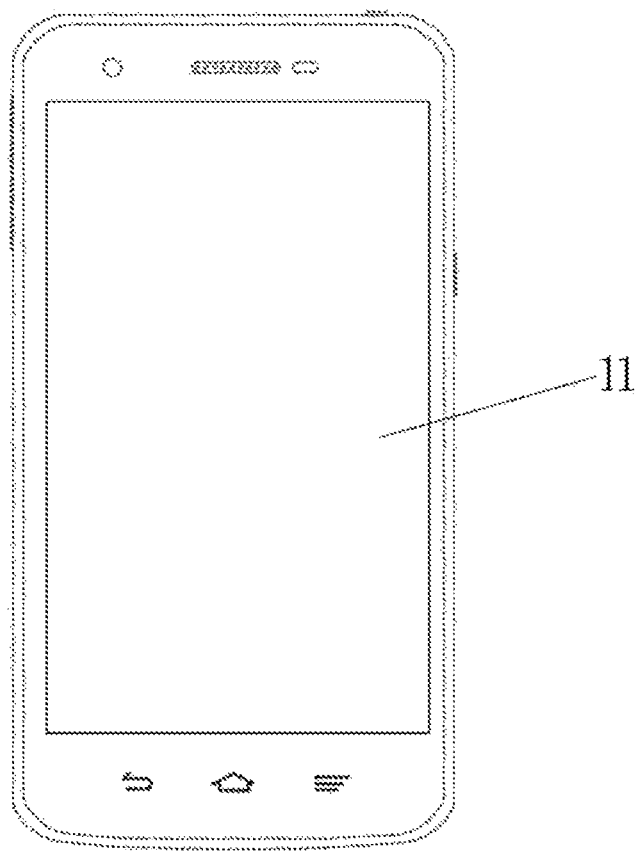
FIG. 3 is a schematic diagram of a display apparatus according to an embodiment of the present disclosure.

In the present disclosure, the organic light-emitting device may be an OLED used in an organic light-emitting display apparatus. The organic light-emitting display apparatus can be display screen of various smart devices, such a mobile phone display screen, a computer display screen, a liquid crystal television display screen, a smart watch display screen, a display panel of smart car, a display screen of Virtual Reality (VR) or Augmented Reality (AR), etc. FIG. 3 is a schematic diagram of a display apparatus according to an embodiment of the present disclosure, in which 11 denotes a mobile phone display screen.

The embodiments of the present disclosure described above are not intended to limit the scope of the present

H077

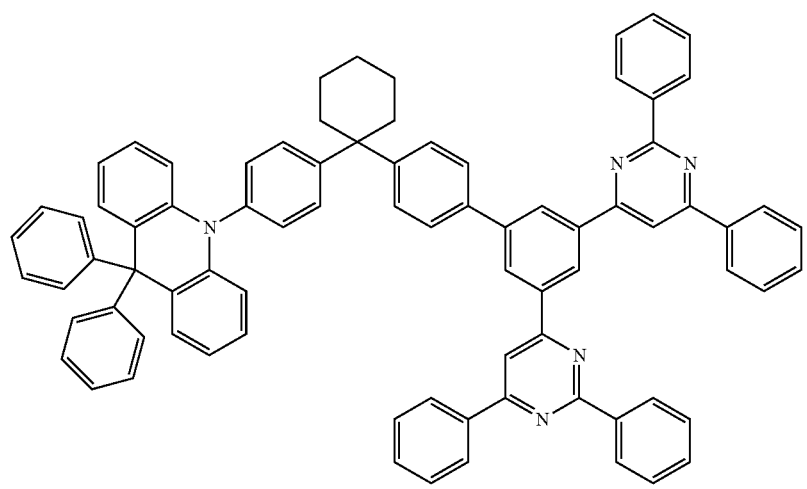

What is claimed is:

1. A compound having a chemical structure represented by a Formula (I):

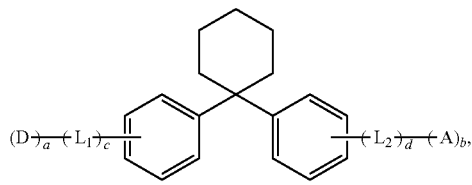

Formula (I)

wherein D represents an electron donor, A represents an electron acceptor, a is a number of an electron donor D, b is a number of an electron acceptor A, and a and b are each 1, 2, or 3 independently;

wherein c is a number of a group $L_1$, d is a number of a group $L_2$, and c and d are each 0, 1, or 2 independently;

wherein the groups $L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocycloalkylene, a substituted or unsubstituted C6-C40 arylene, a substituted or unsubstituted C4-C40 heteroarylene, a substituted or unsubstituted C10-C60 fused arylene, and a substituted or unsubstituted C10-C60 fused heteroarylene;

wherein the electron donor D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and a derivative group thereof, a substituted or unsubstituted C12-C40 diphenylamino and a derivative group thereof, and a substituted or unsubstituted C12-C40 acridinyl and a derivative group thereof; and when acceptor A is selected from nitrogen-containing heterocyclic substituents, the electron donor D is not selected from a substituted or unsubstituted C12-C40 acridinyl and a derivative group thereof; wherein the electron acceptor A is selected from the following substituents:

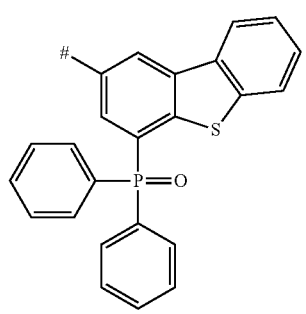

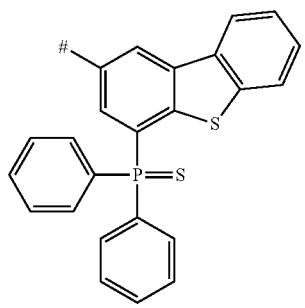

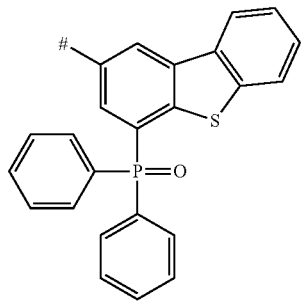

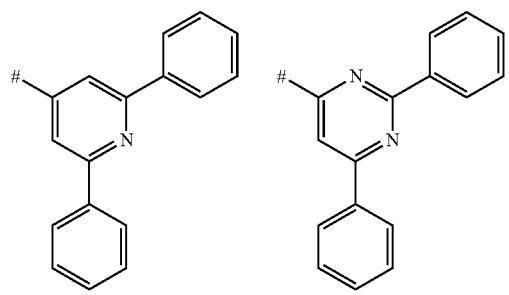

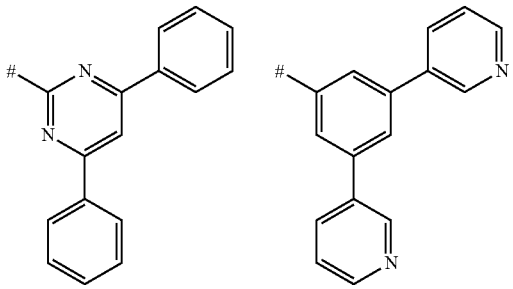

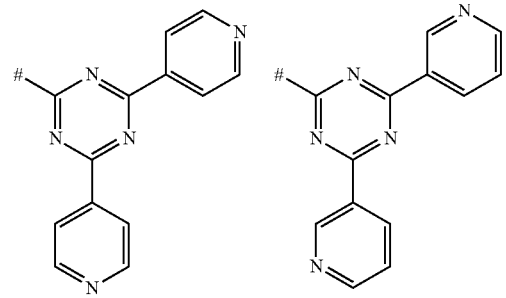

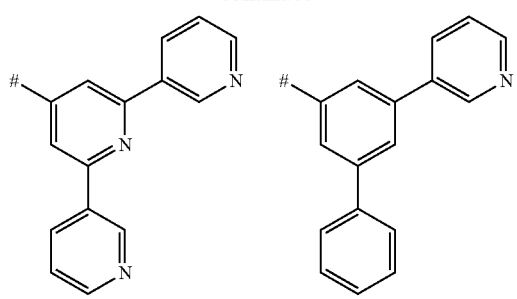
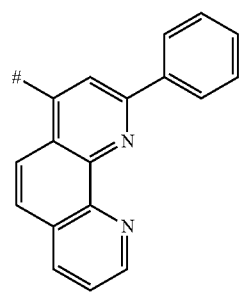
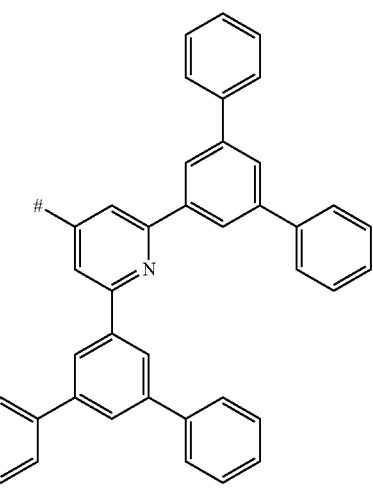
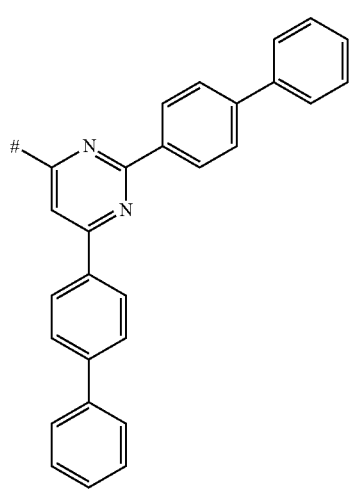
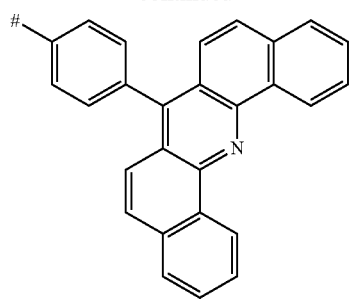
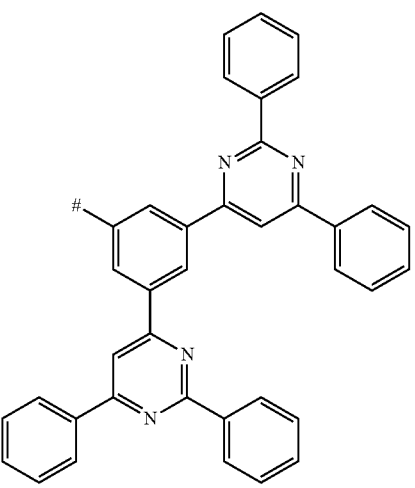
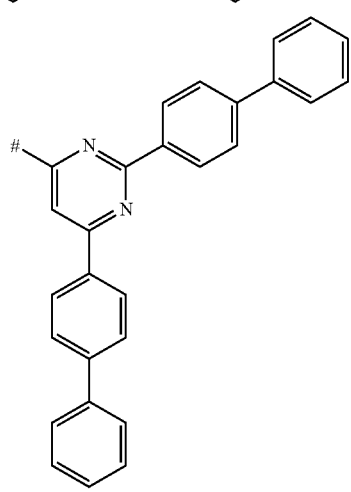
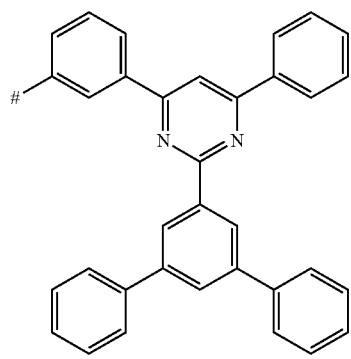

-continued

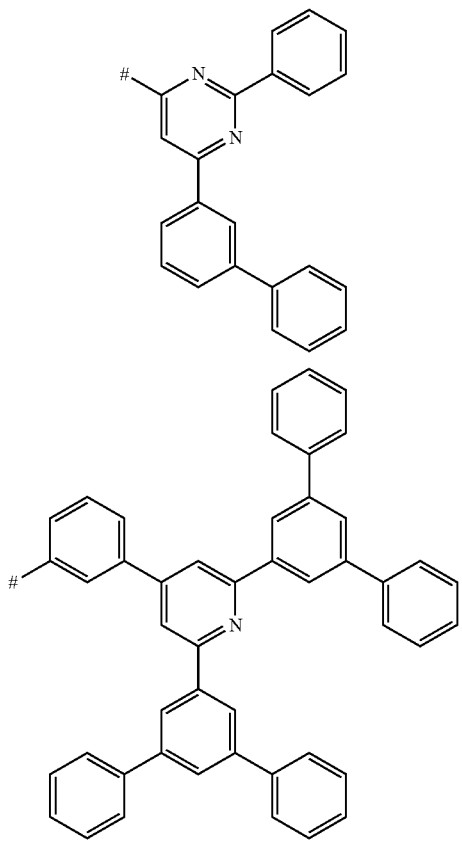

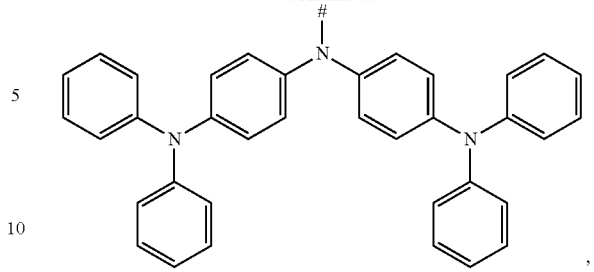

wherein # represents a bonding position.

2. The compound according to claim 1, wherein the electron donor D is further selected from the following groups:

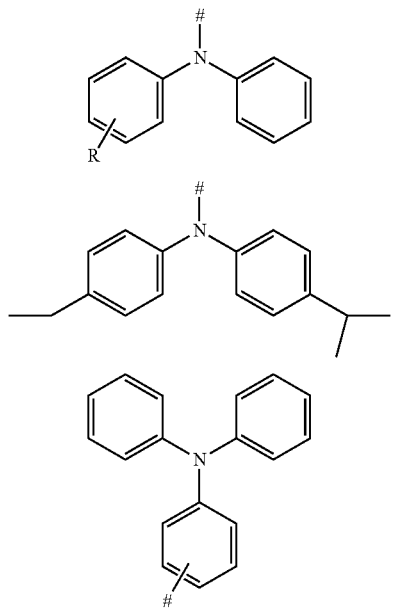

wherein R is selected from the group consisting of hydrogen, a substituted or unsubstituted C1-C20 alkyl, a substituted or unsubstituted silicylene, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C10-C30 fused aryl, and a substituted or unsubstituted C4-C40 heteroaryl.

3. The compound according to claim 1, wherein the electron donor D is further selected from the following groups:

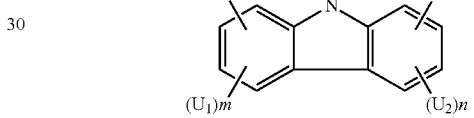
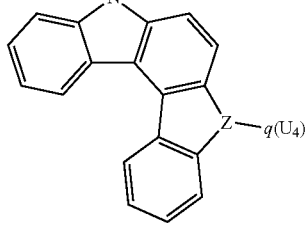
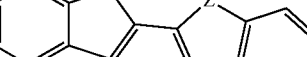
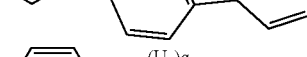
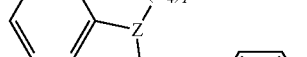
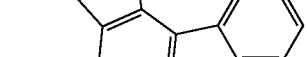

-continued

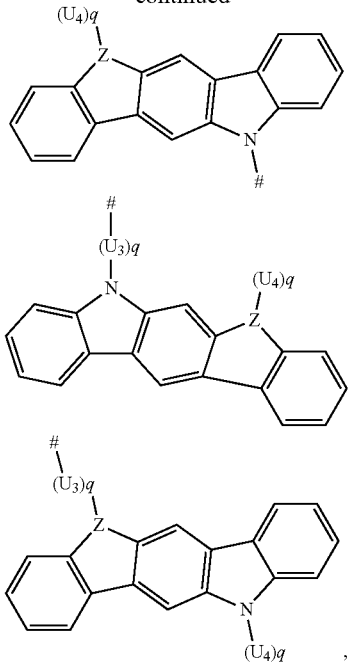

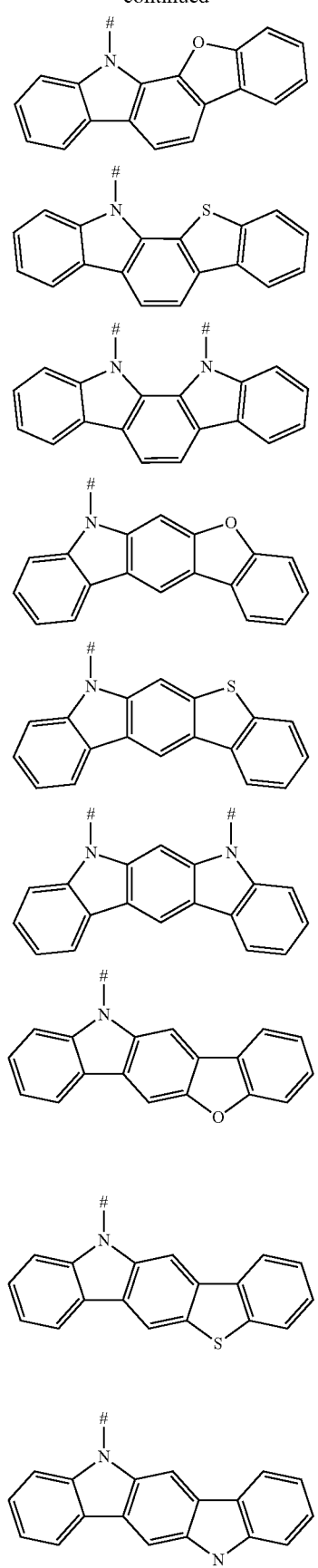

wherein Z is carbon, nitrogen, oxygen, sulfur, or silicon,
m, n and p are each 0, 1, 2, or 3 independently,
$U_1$, $U_2$, $U_3$ and $U_4$ are each independently selected from the group consisting of hydrogen, a substituted or unsubstituted C1-C30 alkyl, a substituted or unsubstituted silicylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl,
when Z is oxygen or sulfur, q is 0, and
represents a bonding position.

4. The compound according to claim 3, wherein the electron donor D is further selected from the following groups:

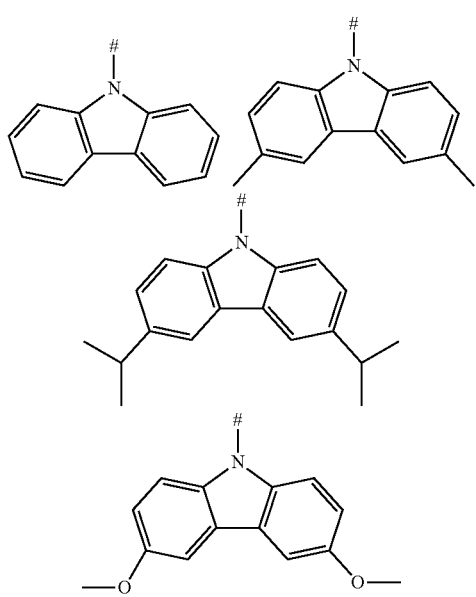

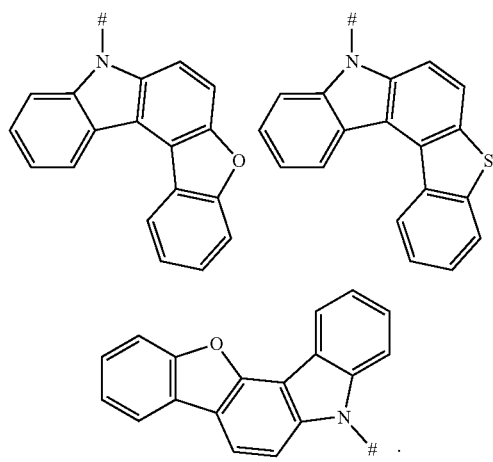

5. The compound according to claim 1, wherein the electron donor D is further selected from the following groups:

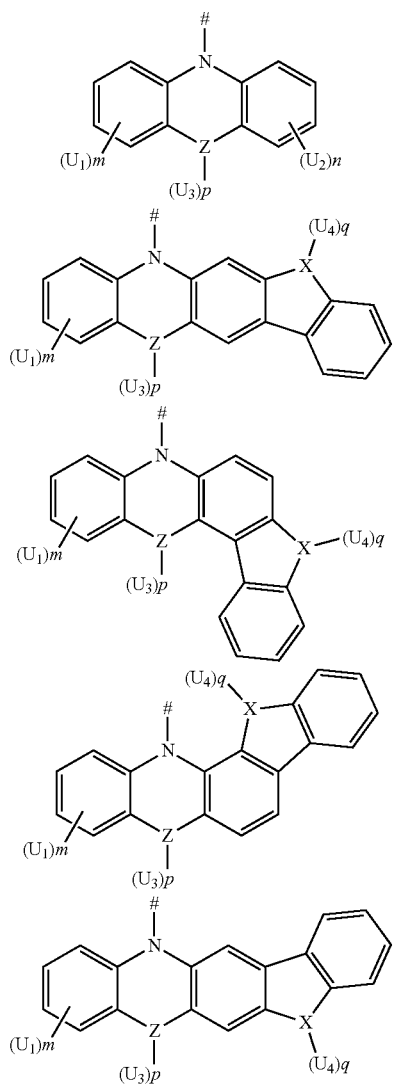

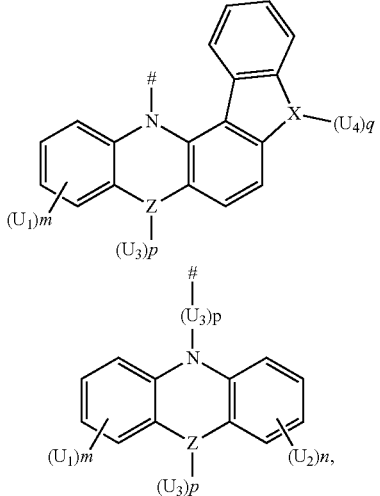

wherein Z is carbon, nitrogen, oxygen, sulfur, or silicon,
X is carbon, nitrogen, oxygen, or sulfur,
m, n, p and p are each 0, 1, 2, or 3 independently,
$U_1$, $U_2$, $U_3$ and $U_4$ are each independently selected from the group consisting of hydrogen, a substituted or unsubstituted C1-C30 alkyl, a substituted or unsubstituted silicylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl,
when Z is oxygen or sulfur, p is 0,
when X is oxygen or sulfur, q is 0, and
represents a bonding position.

6. The compound according to claim 5, wherein the electron donor D is further selected from the following groups:

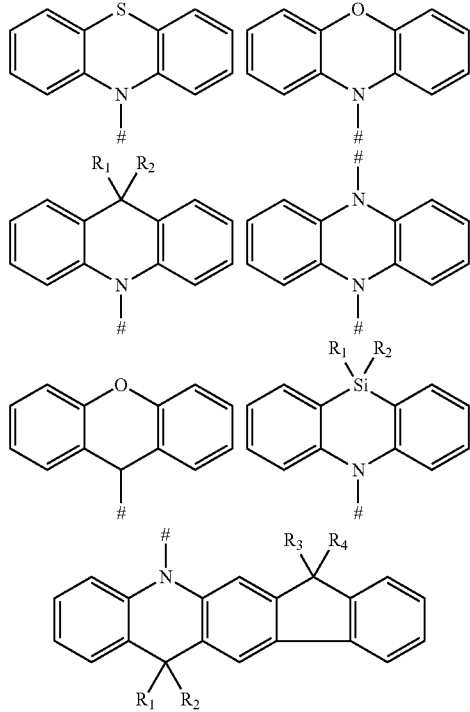

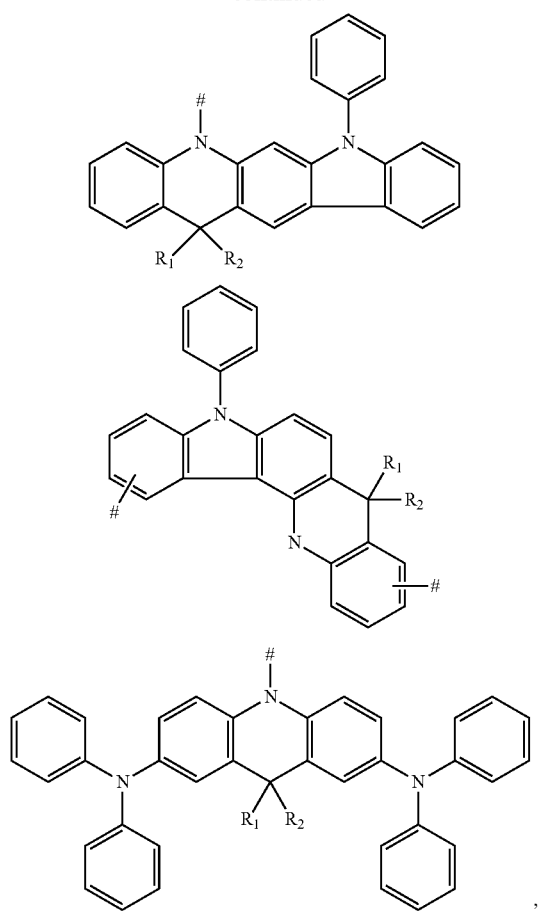

wherein R$_1$, R$_2$, R$_3$ and R$_4$ are each independently selected from the group consisting of hydrogen, a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, and a substituted or unsubstituted C4-C40 heteroaryl.

7. The compound according to claim 1, wherein the compound is further selected from the following compounds:

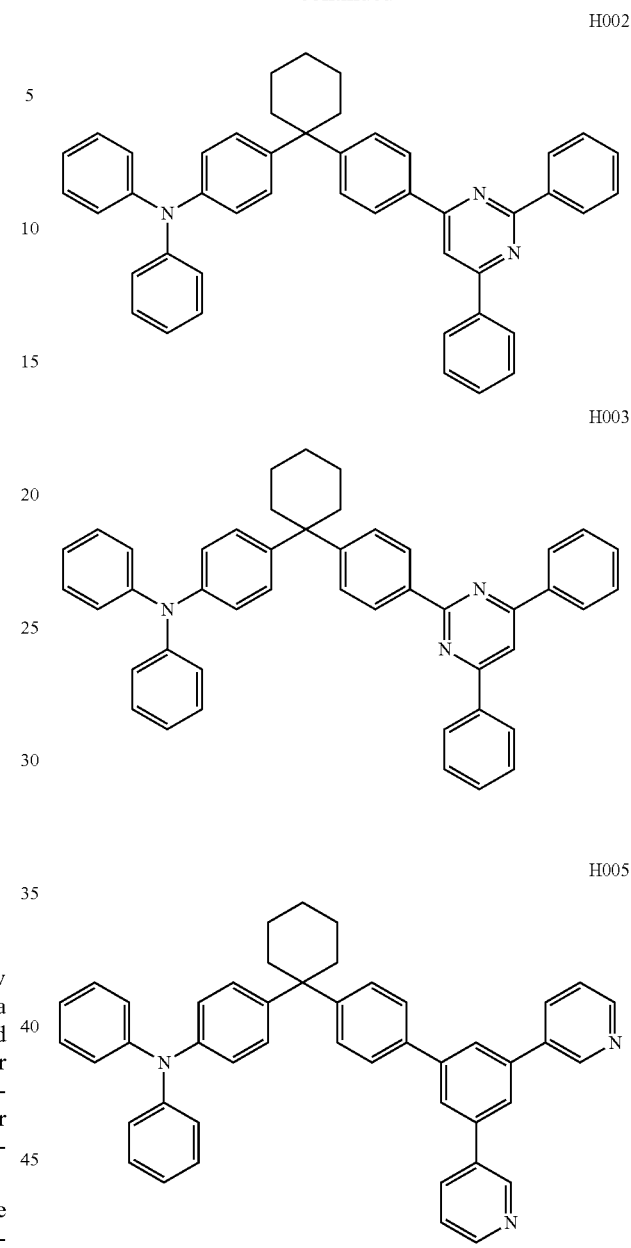

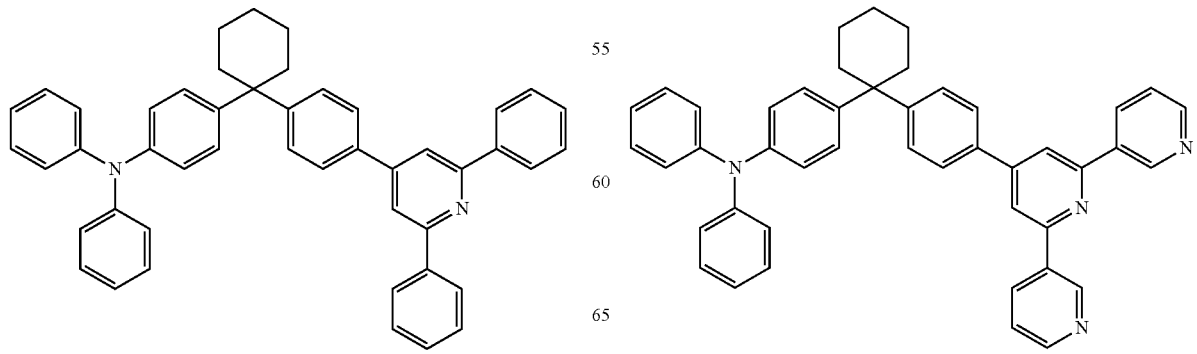

-continued
H007
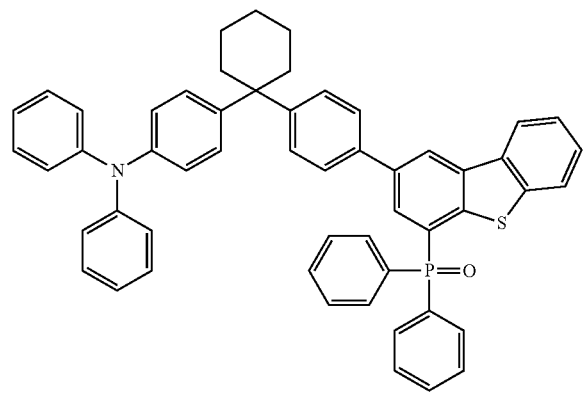
H008
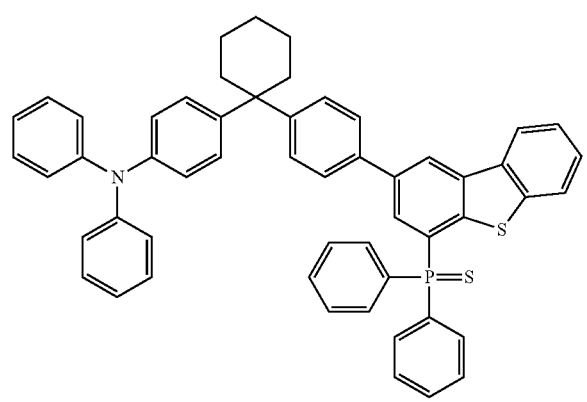
H009
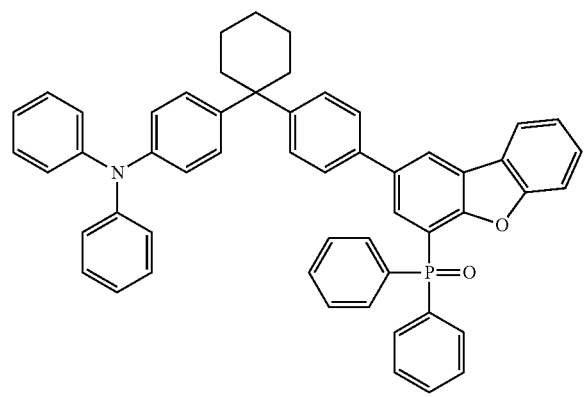
H013
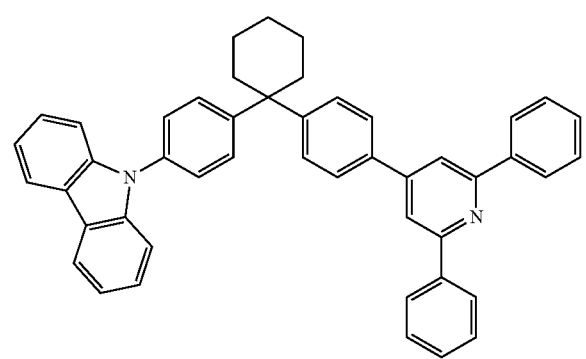
-continued
H014
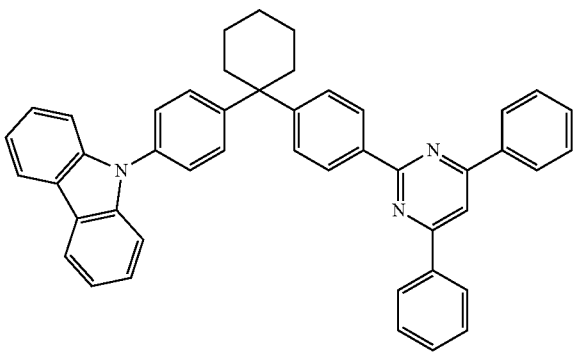
H015
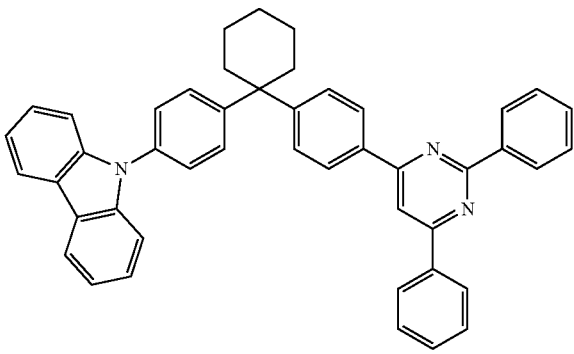
H016
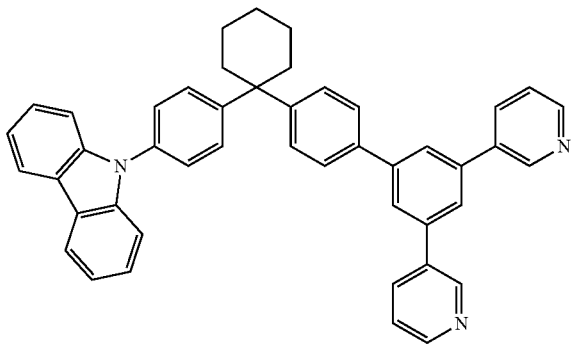
H017
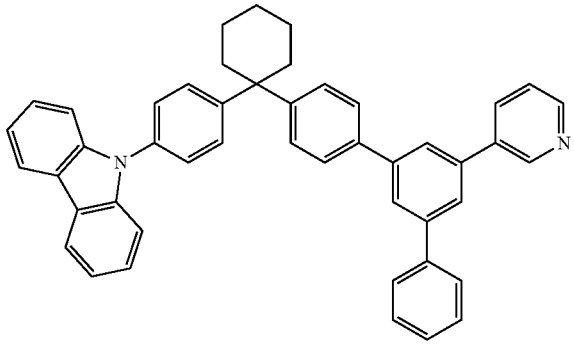

H018
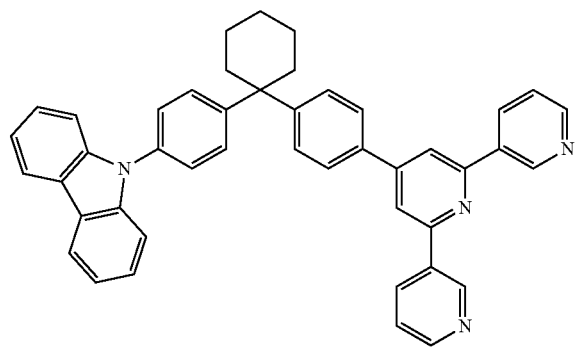
H022
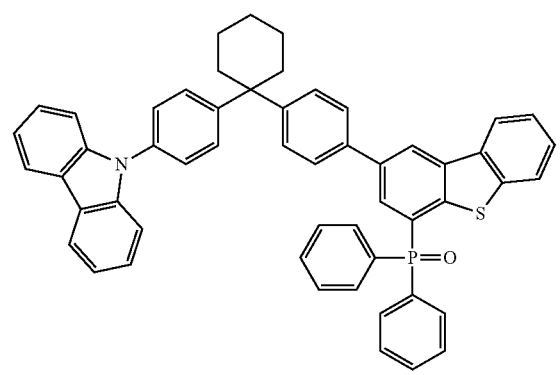
H023
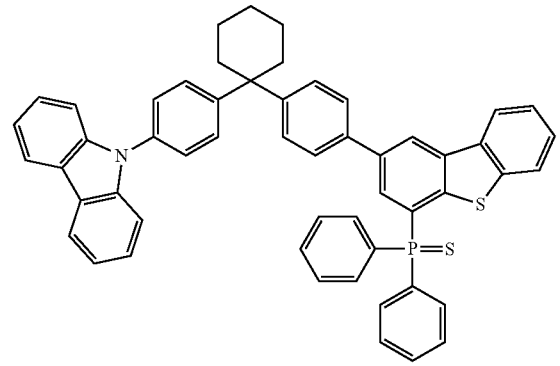
H024
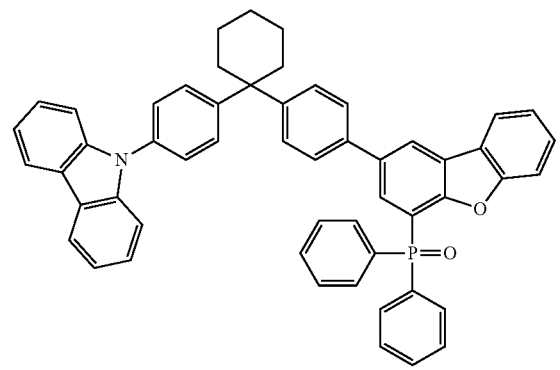
H037
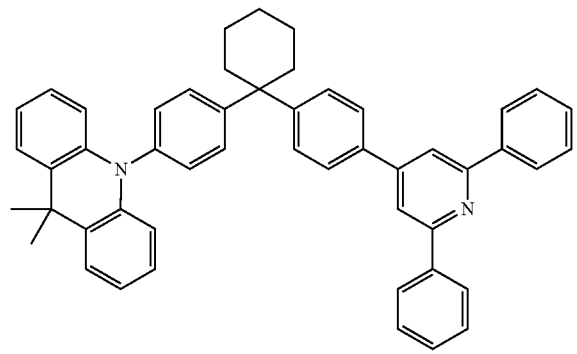
H039
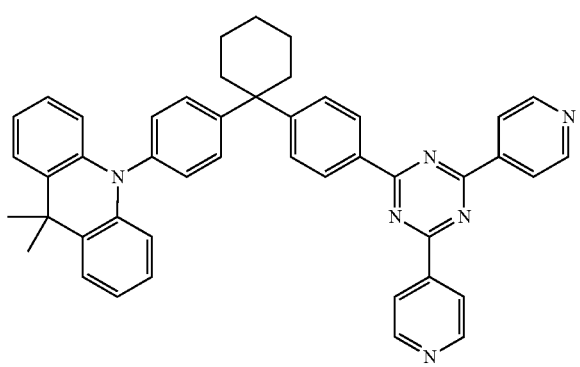
H040
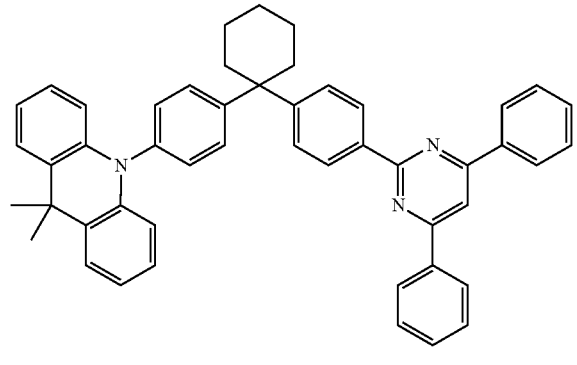
H041
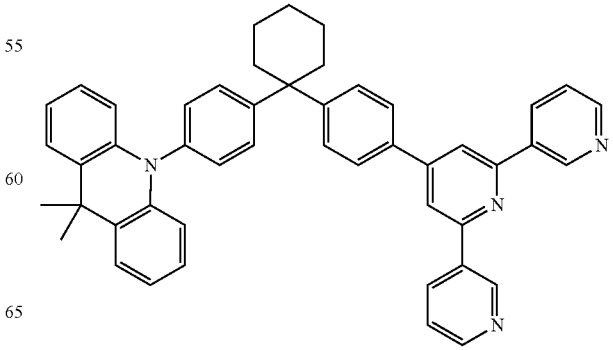

H042
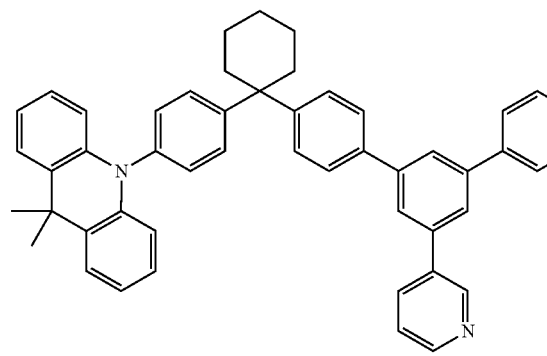
H044
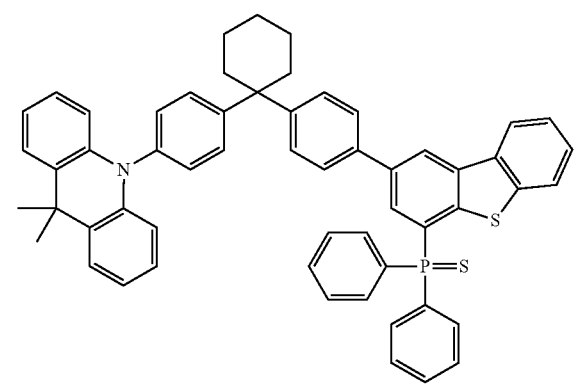
H045
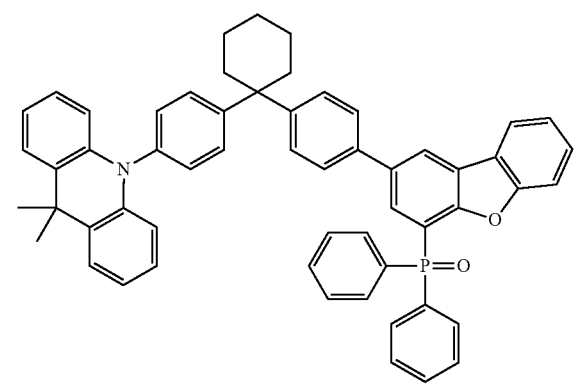
H049
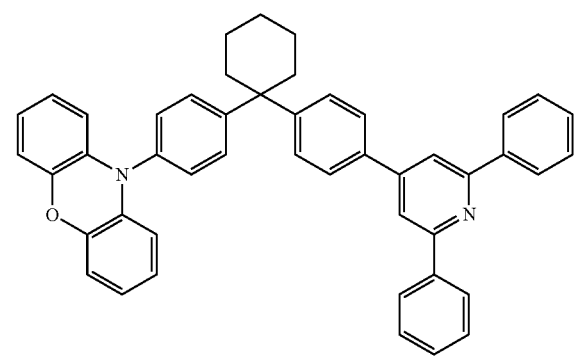
H050
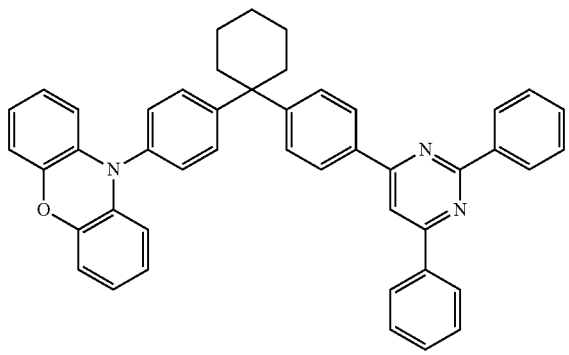
H051
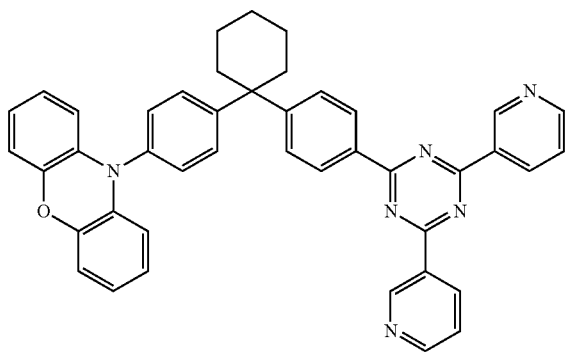
H052
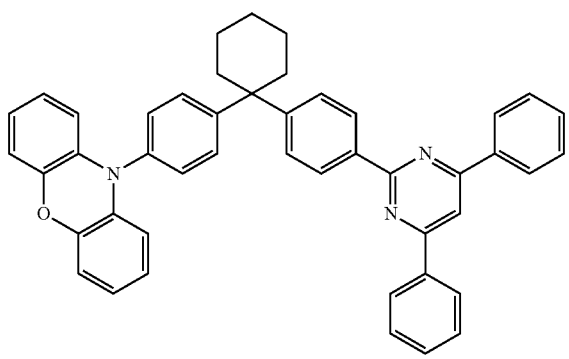
H053
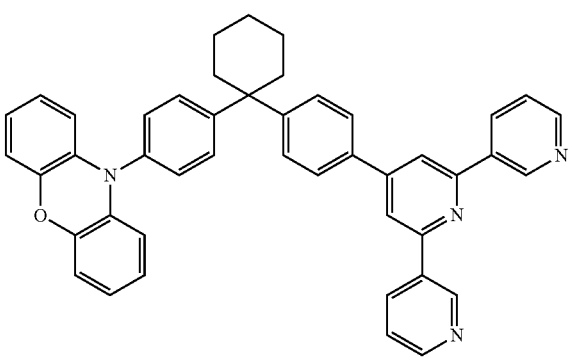

H054
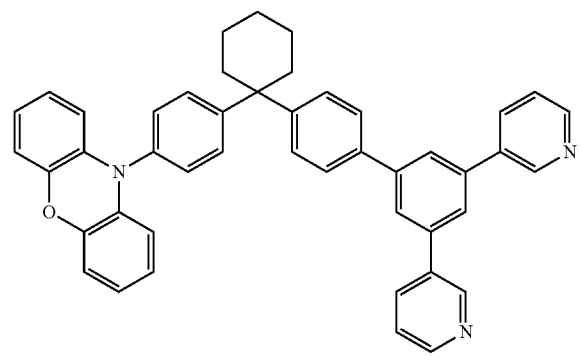
H055
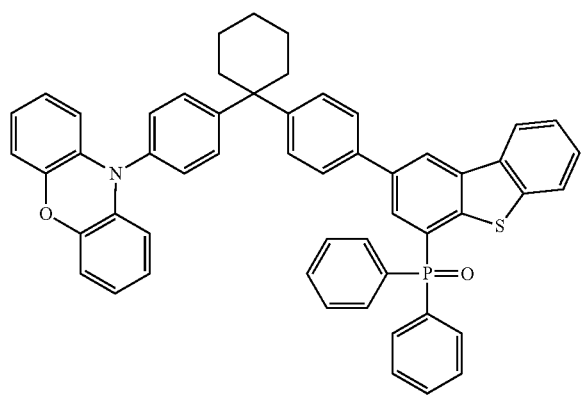
H056
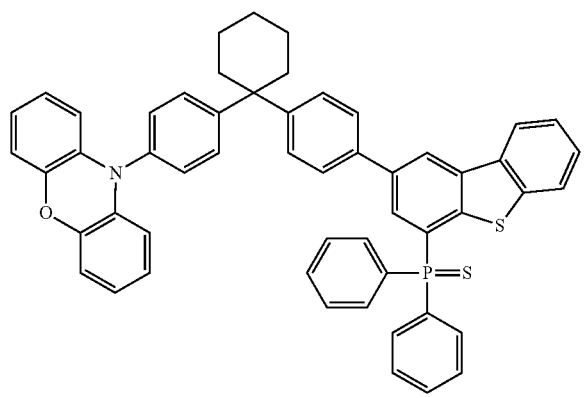
H057
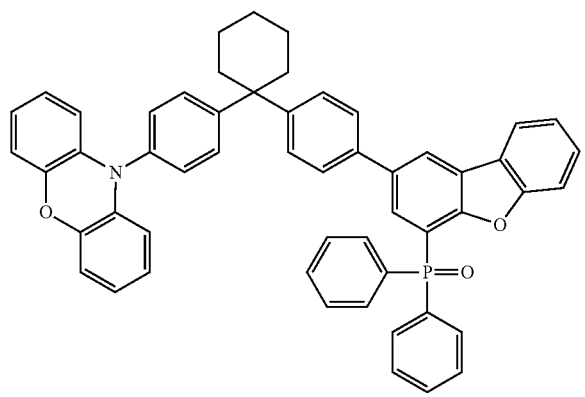
H061
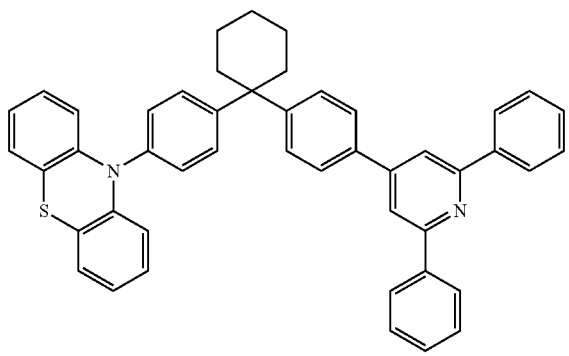
H062
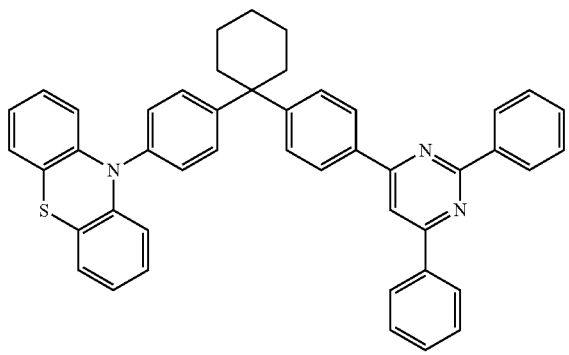
H064
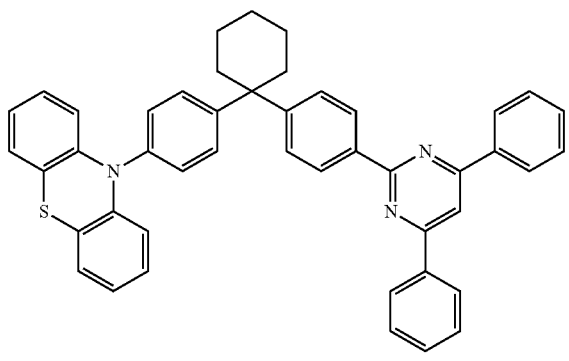
H065
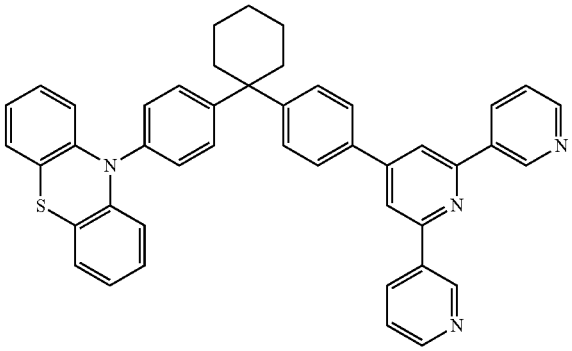

H066
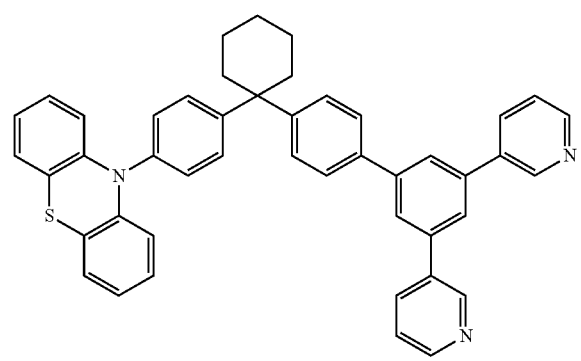
H073
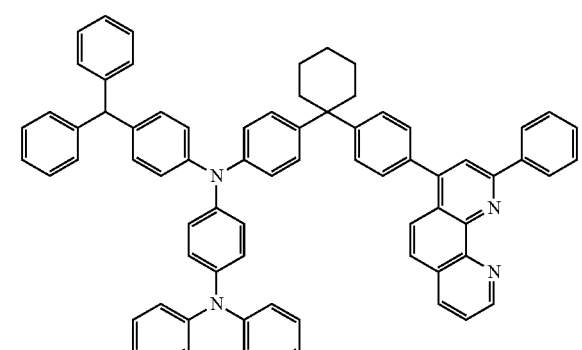
H067
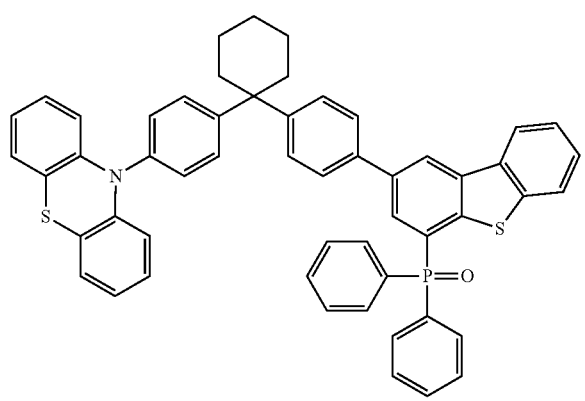
H074
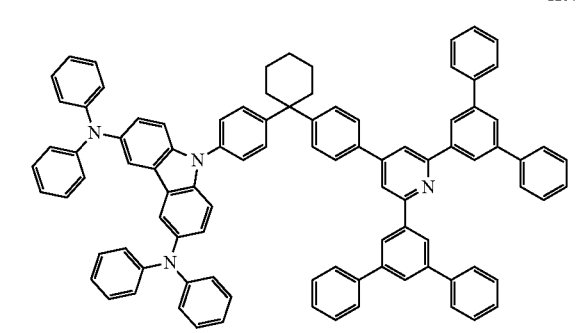
H068
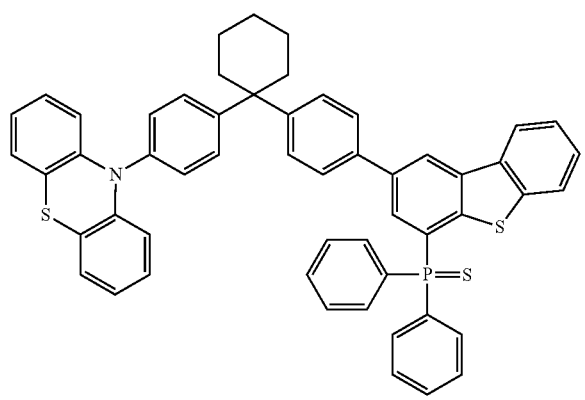
H075
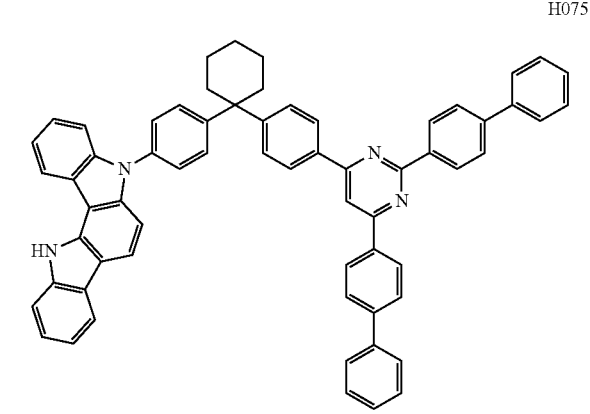
H069
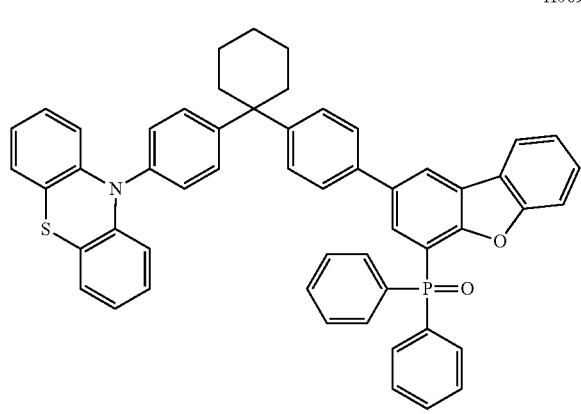
H076
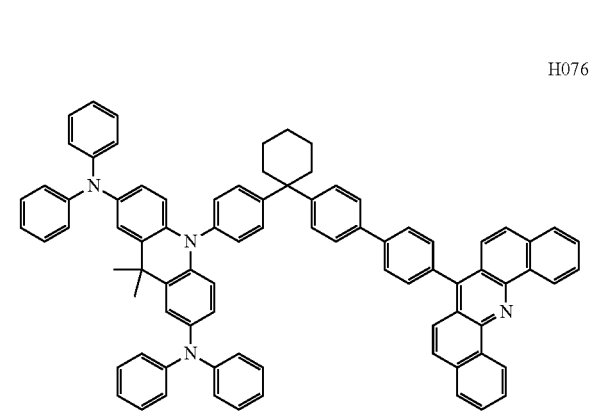

-continued

H077
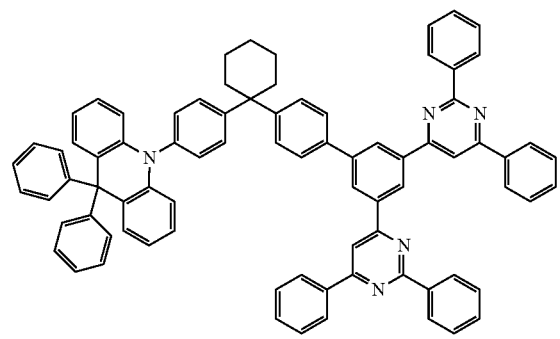

H081
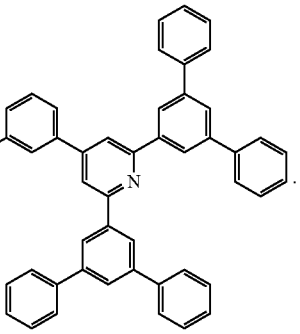

H078
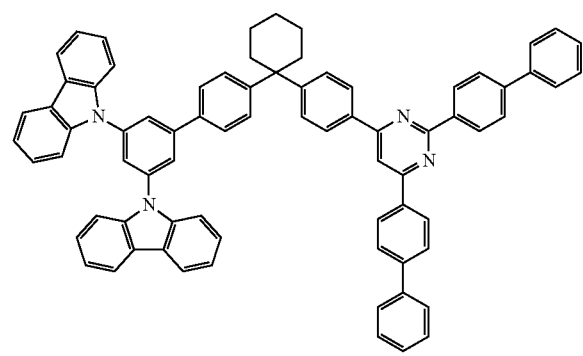

H079
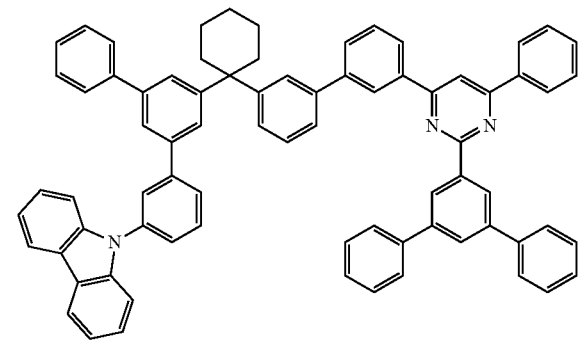

H080
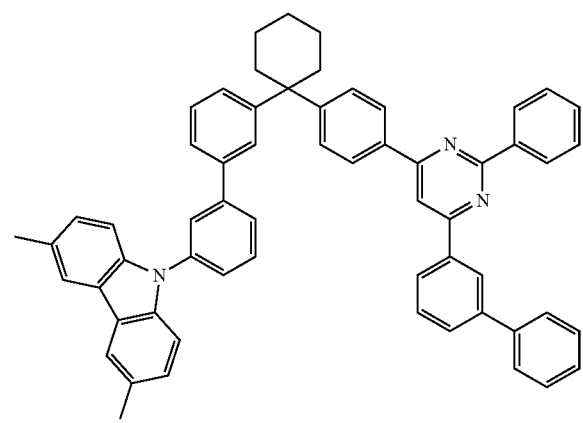

8. A display panel, comprising an organic light-emitting device, wherein the organic light-emitting device comprises an anode, a cathode disposed oppositely to the anode, and a light-emitting layer disposed between the anode and the cathode, wherein
the light-emitting layer comprises a host material and a guest material, and
the host material is one or more compounds having a chemical structure represented by Formula (I):

Formula (I)
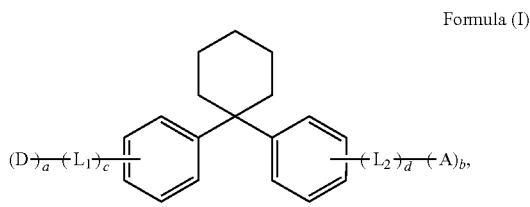

wherein D represents an electron donor, A represents an electron acceptor, a is a number of the electron donor D, b is a number of the electron acceptor A, and a and b are each independently 1, 2, or 3,
c is a number of a group $L_1$, d is a number of a group $L_2$, and c and d are each 0, 1, or 2 independently,
wherein $L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocycloalkylene, a substituted or unsubstituted C6-C40 arylene, a substituted or unsubstituted C4-C40 heteroarylene, a substituted or unsubstituted C10-C60 fused arylene, and a substituted or unsubstituted C10-C60 fused heteroarylene, wherein the electron donor D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and a derivative group thereof, a substituted or unsubstituted C12-C40 diphenylamino and a derivative group thereof, and a substituted or unsubstituted C12-C40 acridinyl and a derivative group thereof, and when acceptor A is selected from nitrogen-containing heterocyclic substituents, the electron donor D is not selected from a substituted or unsubstituted C12-C40 acridinyl and a derivative group thereof;
wherein
the electron acceptor A is selected from the following substituents:
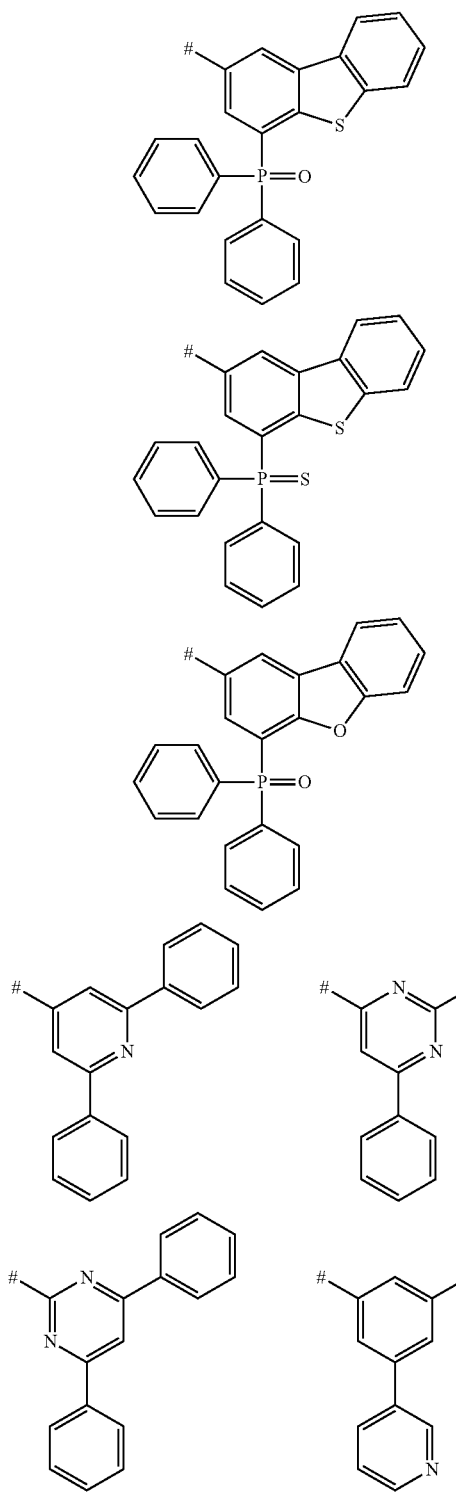
-continued
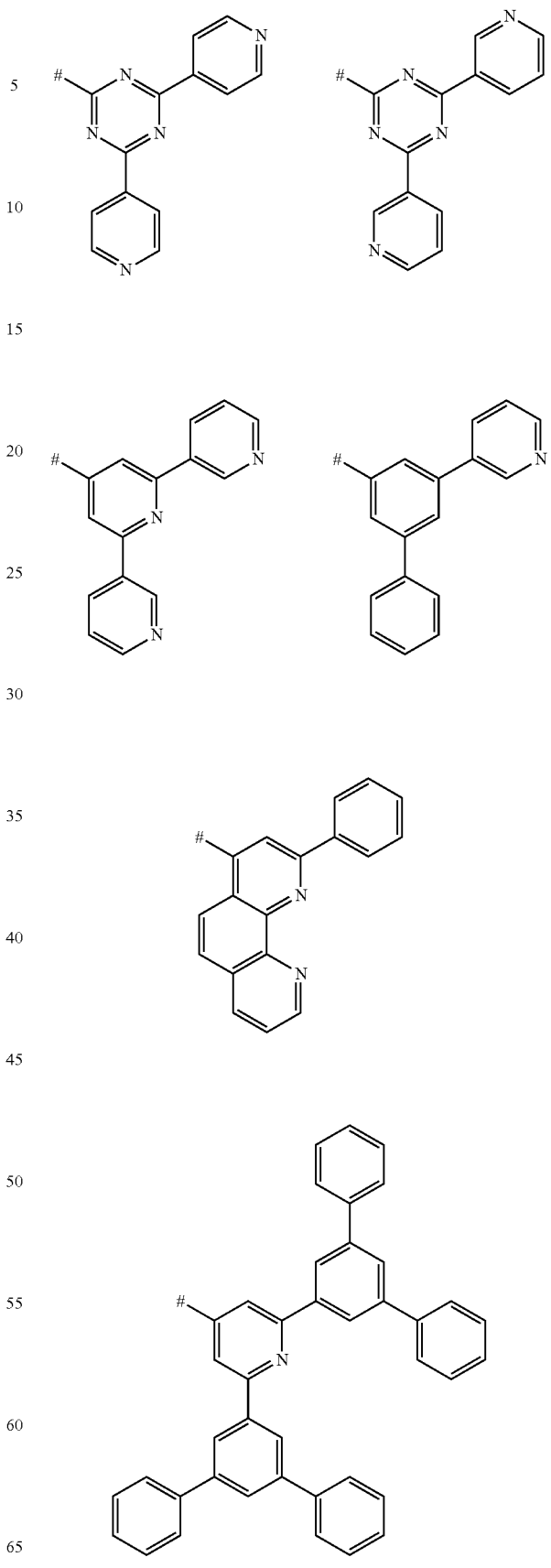

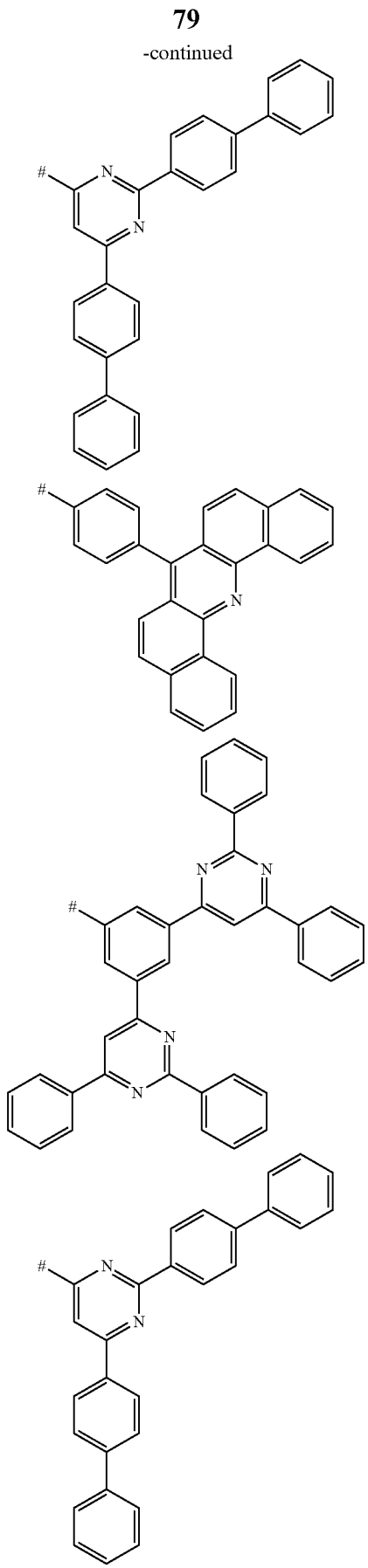

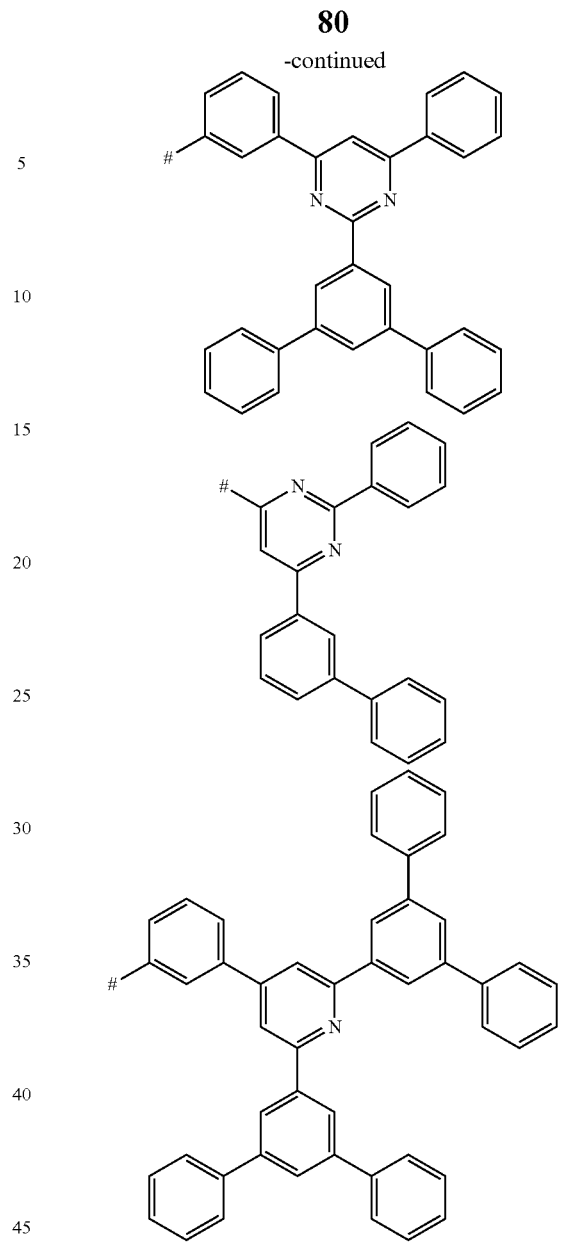

wherein # represents a bonding position.

9. The display panel according to claim 8, wherein a singlet energy level of the host material is higher than a singlet energy level of the guest material, and an energy difference between the singlet energy level of the host material and the singlet energy level of the guest material is less than 0.8 eV, and wherein a triplet energy level of the host material is higher than a triplet energy level of the guest material, and an energy difference between the triplet energy level of the host material and the triplet energy level of the guest material is less than 0.4 eV.

10. The display panel according to claim 8, wherein when the host material of the light-emitting layer is a red-light-emitting material, a triplet energy level of the red-light-emitting material has an energy greater than or equal to 2.2 eV;

when the host material of the light-emitting layer is a green-light-emitting material, a triplet energy level of the green-light-emitting material has an energy greater than or equal to 2.5 eV; and when the host material of the light-emitting layer is a blue-light-emitting material, a triplet energy level of the blue-light-emitting material has an energy greater than or equal to 2.7 eV.

11. The display panel according to claim 8, wherein the organic light-emitting device further comprises one or more of a hole injection layer, a hole transmission layer, an electron blocking layer, a hole blocking layer, an electron transmission layer, and an electron injection layer.

12. The display panel according to claim 9, wherein the organic light-emitting device further comprises one or more of a hole injection layer, a hole transmission layer, an electron blocking layer, a hole blocking layer, an electron transmission layer, and an electron injection layer.

13. The display panel according to claim 10, wherein the organic light-emitting device further comprises one or more of a hole injection layer, a hole transmission layer, an electron blocking layer, a hole blocking layer, an electron transmission layer, and an electron injection layer.

14. A display panel, comprising an organic light-emitting device,
wherein the organic light-emitting device comprises an anode, a cathode disposed oppositely to the anode, a capping layer disposed on a side of the cathode facing away from the anode, and an organic layer disposed between the anode and the cathode;
wherein the organic layer comprises an electron transmission layer, a hole transmission layer, and a light-emitting layer; and
wherein at least one of the capping layer, the electron transmission layer, the hole transmission layer and the light-emitting layer is made of a compound having a chemical structure represented by a Formula (I):

Formula (I)

$$(D)_a{-}(L_1)_c{-}\phantom{X}{-}(L_2)_d{-}(A)_b,$$

wherein D represents an electron donor, A represents an electron acceptor, a is a number of an electron donor D, b is a number of an electron acceptor A, and a and b are each 1, 2, or 3 independently;
wherein c is a number of a group $L_1$, d is a number of a group $L_2$, and c and d are each 0, 1, or 2 independently;
wherein the groups $L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocycloalkylene, a substituted or unsubstituted C6-C40 arylene, a substituted or unsubstituted C4-C40 heteroarylene, a substituted or unsubstituted C10-C60 fused arylene, and a substituted or unsubstituted C10-C60 fused heteroarylene;
wherein the electron donor D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and a derivative group thereof, a substituted or unsubstituted C12-C40 diphenylamino and a derivative group thereof, and a substituted or unsubstituted C12-C40 acridinyl and a derivative group thereof; and when acceptor A is selected from nitrogen-containing heterocyclic substituents, the electron donor D is not selected from a substituted or unsubstituted C12-C40 acridinyl and a derivative group thereof; wherein the electron acceptor A is selected from the following substituents:

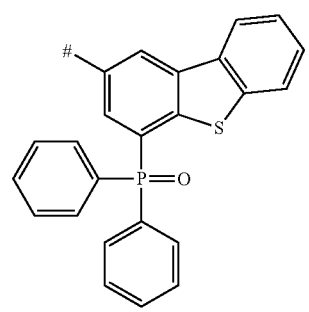

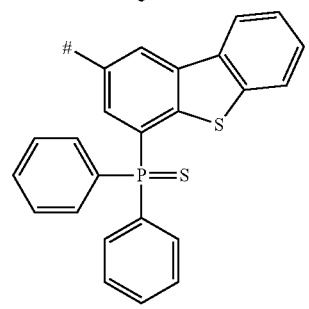

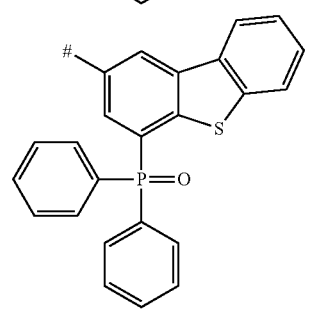

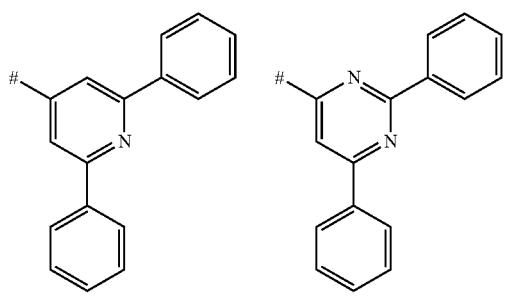

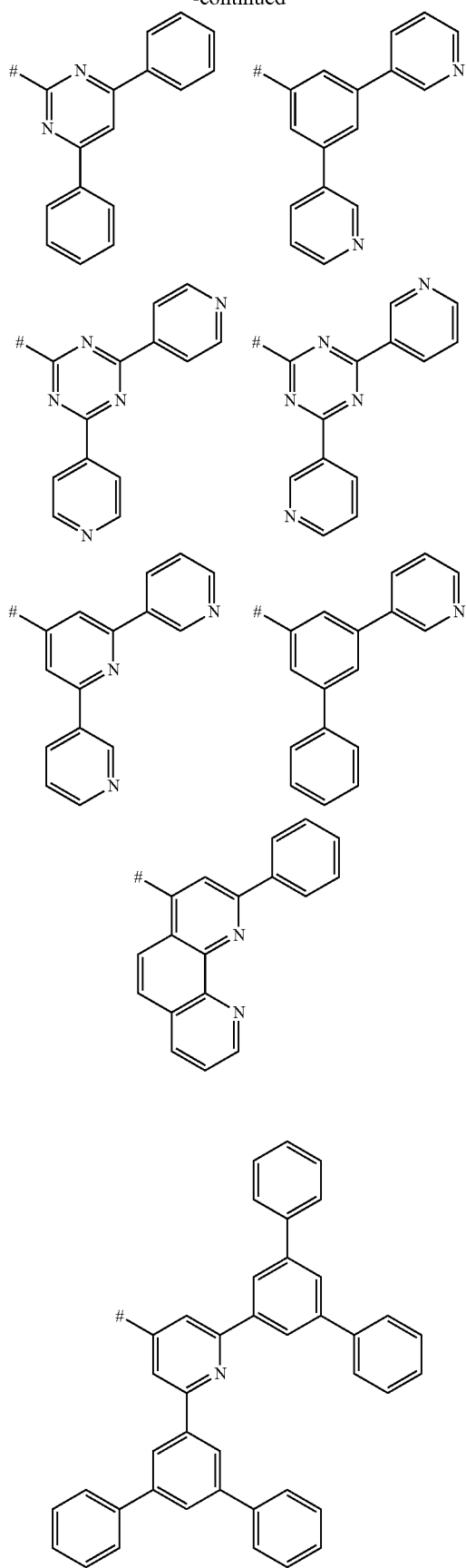
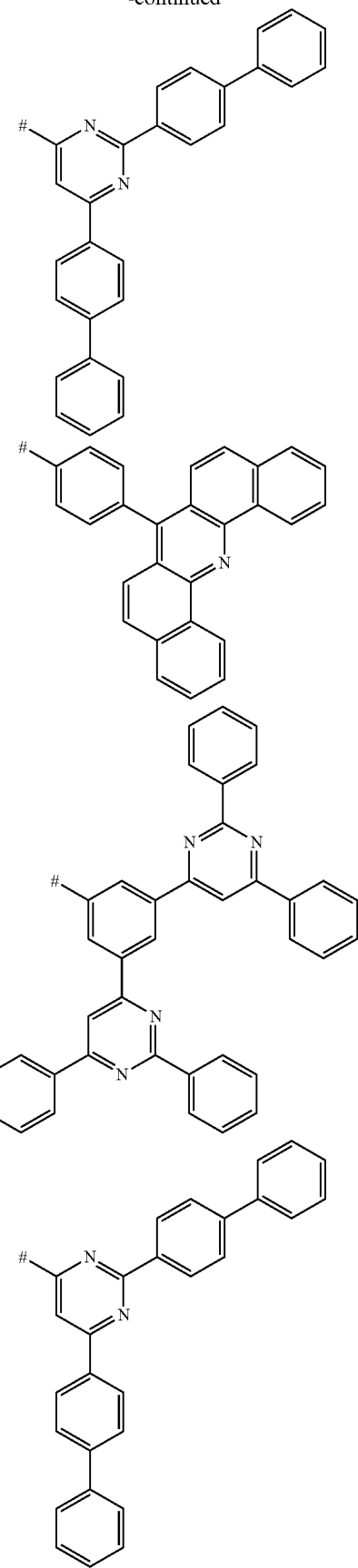

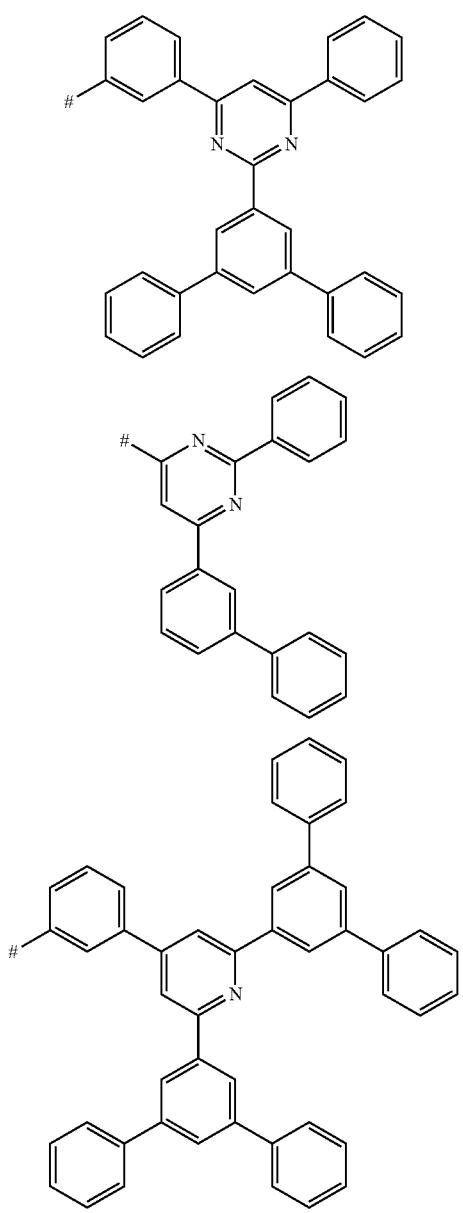
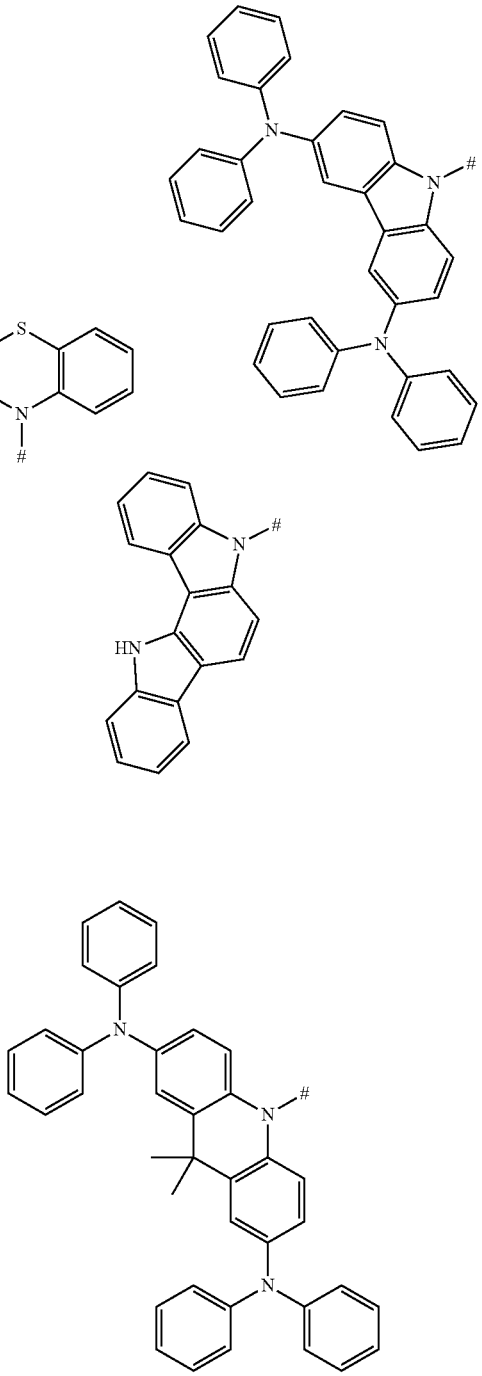
wherein # represents a bonding position.
15. The compound according to claim 1, wherein the electron donor D is further selected from the following substituents:
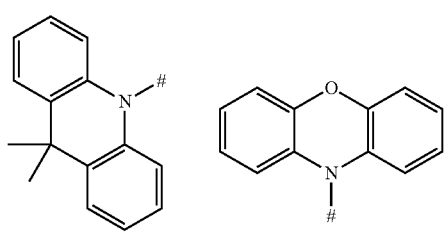
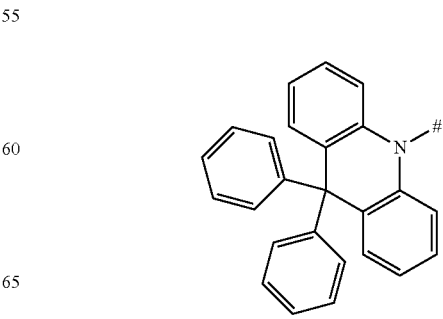

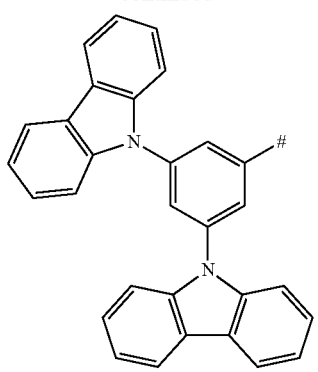
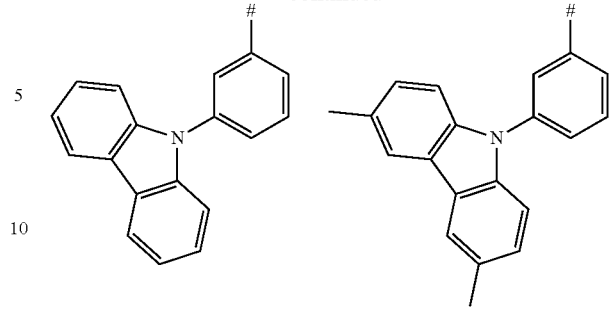
wherein # represents a bonding position.
16. The compound according to claim 7, wherein the compound is as follows:
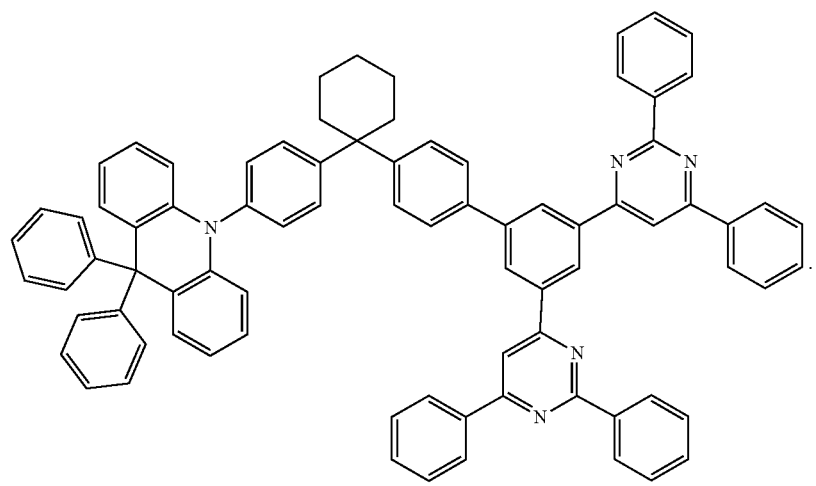
* * * * *